United States Patent [19]

Cassidy et al.

[11] 4,162,324

[45] Jul. 24, 1979

[54] ANTIBIOTICS 890A$_1$ AND 890A$_3$

[75] Inventors: Patrick J. Cassidy, Rahway; Robert T. Goegelman, Linden; Edward O. Stapley, Metuchen, all of N.J.; Sebastian Hernandez, Madrid, Spain

[73] Assignee: Merck & Co., Inc., Rahway, N.J.

[21] Appl. No.: 827,504

[22] Filed: Aug. 25, 1977

Related U.S. Application Data

[63] Continuation of Ser. No. 634,300, Nov. 21, 1975, abandoned.

[51] Int. Cl.$^2$ .................... C07D 487/04; A61K 31/40
[52] U.S. Cl. ............................... 424/274; 260/326.31; 435/121; 435/886
[58] Field of Search .................... 260/326.31; 424/274

[56] References Cited

U.S. PATENT DOCUMENTS 3,950,357 4/1976 Kahan et al. .................. 260/326.31
4,000,161 12/1976 Geogelman et al. ............ 260/326.31

FOREIGN PATENT DOCUMENTS 839324 3/1975 Belgium .................................. 424/274

Primary Examiner—Donald G. Daus
Assistant Examiner—Mary Lee
Attorney, Agent, or Firm—Hesna J. Pfeiffer; James A. Arno; Julian S. Levitt

[57] ABSTRACT

The antibiotics MSD 890A$_1$ and MSD 890A$_3$ and pharmaceutically acceptable salts thereof (hereinafter referred to as antibiotics 890A$_1$ and 890A$_3$) are active against both gram-positive and gram-negative bacteria. The antibiotics are produced by growing species of Streptomyces on suitable fermentation media.

6 Claims, No Drawings

ANTIBIOTICS 890A₁ AND 890A₃

This is a continuation of application Ser. No. 634,300 filed Nov. 21, 1975, now abandoned.

BACKGROUND OF THE INVENTION

The discovery of the remarkable antibiotic properties of penicillin stimulated great interest in this field which has resulted in the finding of many other valuable antibiotic substances such as: other penicillins, cephalosporins, streptomycin, bacitracin, tetracyclines, chloramphenicol, erythromycins and the like. In general the antibacterial activity of each of these antibiotics does not include certain clinically important pathogenic bacteria. For example, some are principally active against only gram-positive types of bacteria. Acquired resistance over the course of widespread use of existing antibiotics in the treatment of bacterial infection has caused a serious resistance problem to arise.

Accordingly, the deficiencies of the known antibiotics have stimulated further research to find other antibiotics which will be active against a wider range of pathogens as well as resistant strains of particular microorganisms.

SUMMARY OF THE INVENTION

This invention relates to new antibiotic agents. More particularly, it is concerned with new antibiotic substances, herein designated 890A$_1$ and 890A$_3$. The invention encompasses the antibiotics in dilute forms, as crude concentrates and in pure forms.

It is an object of the present invention to provide new and useful antibiotics which are highly effective in inhibiting the growth of various gram-negative and gram-positive microorganisms. Another object is to provide a process for the preparation of these novel antibiotic substances by the fermentation of nutrient media with species of Streptomyces. Other objects will be apparent from the detailed description of this invention hereinafter provided.

The novel antibiotic substances of the present invention are produced by growing under controlled conditions new strains of *Streptomyces flavogriseus*.

Based upon extensive taxonomic studies the strains of microorganisms used in the present invention were identified as belonging to the species *Streptomyces flavogriseus* and have been designated MA-4434a and MA-4600a in the culture collection of Merck & Co., Inc., Rahway, N.J. A culture of each thereof has been placed on permanent deposit with the culture collection of the Northern Regional Laboratories, Northern Utilization Research and Development Division, Agricultural Research Service, U.S. Department of Agriculture, Peoria, Ill., and have been assigned accession No. NRRL 8139 and 8140, respectively.

*Streptomyces flavogriseus* NRRL 8139 produces both antibiotics 890A$_1$ and 890A$_3$ which are isolated in substantially pure form from the fermentation broth. *Streptomyces flavogriseus* NRRL 8140 produces antibiotic 890A$_1$ without any detectable amount of 890A$_3$.

The morphological and cultural characteristics of *Streptomyces flavogriseus* NRRL 8139 are set forth in the following table.

Morphology — Sporophores are branching, straight to flexuous chains of spores, forming tufts. Chains are more than 10 spores in length. Spores are spherical to oval — 0.9μ × 1.2μ(970x).

*Cultural Characteristics*

Oatmeal agar
Vegetative growth — Reverse-yellowish tan, parchment-like growth;
Aerial mycelium — Light gray edged with medium gray
Soluble pigment — None.
Czapek Dox agar (sucrose nitrate agar)
Vegetative growth — Reverse-brown edged with dark brown;
Aerial mycelium — Medium gray, velvety;
Soluble pigment — Slight browning of medium.
Egg albumin agar
Vegetative growth — Reverse-yellowish tan edged with brown;
Aerial mycelium — Medium gray mixed with yellowish gray (2dc) and grayed yellow (2db);
Soluble pigment — Light yellowish tan.
Glycerol asparagine agar
Vegetative growth — Reverse-yellowish tan, flat, spreading;
Aerial mycelium — Velvety, light gray with a strong yellowish tone to gray (2dc);
Soluble pigment — None.
Inorganic salts-starch agar
Vegetative growth — Reverse — brown;
Aerial mycelium — Medium gray, velvety;
Soluble pigment — Light yellowish-tan.
Yeast extract-dextrose + salts agar
Vegetative growth — Reverse-brown edged with very dark brown;
Aerial mycelium — Dark gray mixed with a light gray, velvety;
Soluble pigment — None.
Yeast extract-malt extract agar
Vegetative growth — Reverse-dark brown;
Aerial mycelium — Dark gray, velvety;
Soluble pigment — None.
Skim milk agar
Vegetative growth — Tan;
Aerial mycelium — Sparse, grayish;
Soluble pigment — Slight browning of medium;
Hydrolysis of casein — Good.
Litmus milk
Vegetative growth — Moderate growth ring, dark tan;
Aerial mycelium — None;
Color — Purple;
Coagulation and/or peptonization — Complete peptonization; becoming alkaline, pH 8.2.
Skim milk
Vegetative growth — Moderate growth ring, tan;
Aerial mycelium — None;
Soluble pigment — Tan;
Coagulation and/or peptonization — Complete peptonization; becoming alkaline, pH 8.0.
Tyrosine agar
Vegetative growth — Reverse-dark brown;
Aerial mycelium — Dark gray;
Soluble pigment — Slight browning of medium;
Decomposition of tyrosine — None.
Peptone-iron-yeast extract agar
Vegetative growth — Tan;
Aerial mycelium — Sparse, grayish;
Soluble pigment — None;
Melanin — None;
H$_2$S production — None.

Nutrient agar
Vegetative growth — Reverse-light grayish brown edged with darker gray-brown;
Aerial mycelium — Light gray edged with dark gray;
Soluble pigment — None.
Nutrient starch agar
Vegetative growth — Tan edged with gray
Aerial mycelium — Medium gray edged with dark gray;
Soluble pigment — None;
Hydrolysis of starch — Good
Nutrient gelatin agar
Vegetative growth — Colorless edged with dark gray;
Aerial mycelium — Grayish-white;
Soluble pigment — None;
Liquefaction of gelatin — Good.
Potato plug
Vegetative growth — Good growth, heavily wrinkled;
Aerial mycelium — Gray to greenish-gray;
Soluble pigment — Slight browning of medium.
Loeffler's Blood serum
Vegetative growth — Cream-colored;
Aerial mycelium — None;
Soluble pigment — None;
Liquefaction — None.
Gelatin stabs
Vegetative growth — Cream-colored;
Aerial mycelium — None;
Soluble pigment — None;
Liquefaction of gelatin — Good.

All of the readings reported above were taken after three weeks incubation at 28° C. unless noted otherwise. The pH of the media used in these studies was approximately neutral, namely, pH 6.8–7.2. The color designations used in the description are in accordance with the definitions of the *Color Harmony Manual*, 4th Edition (1958), Container Corporation of America, Chicago, Illinois.

*Streptomyces flavogriseus* NRRL 8139 was also tested for its ability to utilize or assimilate various carbohydrates. For this purpose, the microorganism was grown on basal synthetic medium (Pridham and Gottlieb) containing 1% of the carbohydrate at 28° C. for three weeks. The pH of the media employed in the study was approximately neutral (6.8–7.2). Table I shows the utilization of these carbohydrate sources by *Streptomyces flavogriseus* NRRL 8139, + indicating good growth, ± poor growth, and − no growth on the particular carbohydrate.

TABLE I

| Glucose | + | Maltose | + |
|---|---|---|---|
| Arabinose | + | Mannitol | + |
| Cellulose | − | Mannose | + |
| Fructose | + | Raffinose | − |
| Inositol | − | Rhamnose | + |
| Lactose | + | Sucrose | ± |
| Xylose | + | | |

The amount of growth with change in temperature and the oxygen requirement by the microorganism is as follows:
Temperature range (Yeast extract-dextrose + salts agar);
28° C. — Good
37° C. — Good vegetative growth; no aerial hyphae
50° C. — No growth
Oxygen requirement (Stab culture in yeast extract-dextrose + salts agar);
Aerobic The morphological and cultural characteristics of *Streptomyces flavogriseus* NRRL 8140 are set forth in the following table.

Morphology — Sporophores are branching, straight to flexuous chains of spores, forming tufts. Chains are more than 10 spores in length. Spores are spherical to oval — $0.9\mu \times 1.2\mu$ (970x).

*Cultural Characteristics*

Oatmeal agar
Vegetative growth — Reverse — yellowish tan edged with dark brown;
Aerial mycelium — Light gray edged with medium gray;
Soluble pigment — None.
Czapek Dox agar (sucrose nitrate agar)
Vegetative growth — Reverse — brown edged with dark brown;
Aerial mycelium — Medium gray, velvety;
Soluble pigment — None.
Egg albumin agar
Vegetative growth — Reverse — grayish tan with sections of strong yellow tan;
Aerial mycelium — Sections of medium gray, grayish white and yellowish gray (2dc);
Soluble pigment — Very light tan.
Glycerol asparagine agar
Vegetative growth — Yellowish tan;
Aerial mycelium — Sparse, grayish;
Soluble pigment — None.
Inorganic salts-starch agar
Vegetative growth — Reverse — grayish cream;
Aerial mycelium — Medium gray, velvety;
Soluble pigment — None.
Yeast extract-dextrose + salts agar
Vegetative growth — Reverse — dark brown;
Aerial mycelium — Dark gray mixed with a light gray, velvety;
Soluble pigment — None.
Yeast extract-malt extract agar
Vegetative growth — Reverse — dark brown;
Aerial mycelium — Dark Gray, velvety;
Soluble pigment — None.
Peptone-iron-yeast extract agar
Vegetative growth — Tan;
Aerial mycelium — None;
Soluble pigment — None;
Melanin — None;
$H_2S$ production — None.
Nutrient agar
Vegetative growth — Light tan;
Aerial mycelium — None.
Soluble pigment — None.
Nutrient starch agar
Vegetative growth — Cream-colored;
Aerial mycelium — None;
Soluble pigment — None;
Hydrolysis of starch — Good.
Nutrient gelatin agar
Vegetative growth — Cream-colored;
Aerial mycelium — None;
Soluble pigment — None;
Liquefaction of gelatin — Good.
Gelatin stabs Vegetative growth — Tan;
Aerial mycelium — None;
Soluble pigment — None;
Liquefaction of gelatin — Complete.
Skim milk agar
Vegetative growth — Tan;
Aerial mycelium — None;
Soluble pigment — None;
Hydrolysis of casein — Good.
Litmus milk
Vegetative growth — Tan growth ring
Aerial mycelium — None;
Color — Brownish purple;
Coagulation and/or peptonization — Complete peptonization, becoming alkaline, pH 8.0.
Skim milk
Vegetative growth — Tan, moderate growth ring;
Aerial mycelium — None;
Soluble pigment — Light brown;
Coagulation and/or peptonization — Complete peptonization, becoming alkaline, pH 8.5.
Potato plug
Vegetative growth — Good, tan colored;
Aerial mycelium — Very sparse, whitish;
Soluble pigment — None.
Loeffler's Blood serum
Vegetative growth — Cream-colored;
Aerial mycelium — None;
Soluble pigment — None;
Liquefaction — None.
Tyrosine agar
Vegetative growth — Tan;
Aerial mycelium — None;
Soluble pigment — Slight browning of medium;
Decomposition of tyrosine — Very slight.

All of the readings reported above were taken after three weeks incubation at 28° C. unless noted otherwise. The pH of the media used in these studies was approximately neutral, namely pH 6.8–7.2. The color designations used in the description are in accordance with the definitions of the *Color Harmony Manual*, 4th Edition (1958), Container Corporation of America, Chicago, Illinois.

*Streptomyces flavogriseus* NRRL 8140 was also tested for its ability to utilize or assimilate various carbohydrates. For this purpose, the microorganism was grown on basal synthetic medium (Pridham and Gottlieb) containing 1% of the carbohydrate at 28° C. for three weeks. The pH of the media employed in the study was approximately neutral (6.8–7.2) Table II shows the utilization of these carbohydrate sources by *Streptomyces flavogriseus* NRRL 8140 + indicating good growth, ± poor growth, and — no growth on the particular carbohydrate.

TABLE II

| Glucose | + | Maltose | + |
|---|---|---|---|
| Arabinose | + | Mannitol | + |
| Cellulose | − | Mannose | + |
| Fructose | + | Raffinose | ± |
| Inositol | ± | Rhamnose | + |
| Lactose | + | Sucrose | ± |
| Xylose | + | | |

The amount of growth with change in temperature and the oxygen requirement by the microorganism is as follows:

Temperature range (Yeast extract-dextrose + salts agar);

28° C. — Good
37° C. — Moderate vegetative growth; no aerial hyphae
50° C. — No growth Oxygen requirement (Stab culture in yeast extract-dextrose + salts agar);
Aerobic It is to be understood that for the production of new antibiotics of this invention, the present invention is not limited to the organism, *Streptomyces flavogriseus* or to organisms fully answering the above growth and microscopic characteristics which are given for illustrative purposes. In fact, it is desired and intended to include the use of mutants produced from the described organism by various means, such as X-radiation, ultra-violet radiation, nitrogen mustard, phage exposure and the like.

The novel antibiotics of the invention, 890A$_1$ and 890A$_3$, are produced during the aerobic fermentation, under controlled conditions, of suitable aqueous nutrient media inoculated with strains of the organism, *Streptomyces flavogriseus*. Aqueous media, such as those employed for the production of other antibiotics are suitable for producing 890A$_1$ and 890A$_3$. Such media contain sources of carbon, nitrogen and inorganic salts assimilable by the microorganism.

In general, carbohydrates such as sugars, for example, dextrose, glucose, fructose, maltose, sucrose, xylose, mannitol and the like and starches such as dextrin or such as grains, for example, oats, rye, cornstarch, corn meal and the like can be used either alone or in combination as sources of assimilable carbon in the nutrient medium. The exact quantity of the carbohydrate source or sources utilized in the medium depend in part upon the other ingredients of the medium but, in general, the amount of carbohydrate usually varies between about 1% and 6% by weight of the medium. These carbon sources can be used individually, or several such carbon sources may be combined in the medium. In general, many proteinaceous materials may be used as nitrogen sources in the fermentation process. Suitable nitrogen sources include, for example, yeast hydrolysates, primary yeast, soybean meal, cottonseed flour, hydrolysates of casein, corn steep liquor, distiller's solubles or tomato paste and the like. The sources of nitrogen, either alone or in combination, are used in amounts ranging from about 0.2% to 6% by weight of the aqueous medium.

Among the nutrient inorganic salts which can be incorporated in the culture media are the customary salts capable of yielding sodium, potassium, ammonium, calcium, magnesium, phosphate, sulfate, chloride, carbonate, and like ions. Also included are trace metals such as cobalt, manganese and iron.

It should be noted that the media described in the Examples are merely illustrative of the wide variety of media which may be employed, and are not intended to be limitative.

The fermentation is carried out at temperatures ranging from about 20° C. to 37° C.; however, for optimum results it is preferable to conduct the fermentation at temperatures of from about 23° C. to 28° C. The initial pH of the nutrient media suitable for growing strains of the *Streptomyces flavogriseus* culture and producing antibiotics 890A$_1$ and 890A$_3$ can vary from about 6.0 to 8.0.

Although the novel antibiotics 890A$_1$ and 890A$_3$ are produced by both surface and submerged cultures, it is preferred to carry out the fermentation in the submerged state.

A small scale fermentation of the antibiotic is conveniently carried out by inoculating a suitable nutrient medium with the antibiotic-producing culture and, after transfer to a production medium, permitting the fermentation to proceed at a constant temperature of about 28° C. on a shaker for several days.

The fermentation is initiated in a sterilized flask of nutrient medium via one or more stages of seed development. The nutrient medium for the seed stage may be any suitable combination of carbon and nitrogen sources. The seed flask is shaken in a constant temperature chamber at about 28° C. for one day, or until growth is satisfactory, and some of the resulting growth is used to inoculate either a second stage seed or the production medium. Intermediate stage seed flasks, when used, are developed in essentially the same manner; that is, part of the contents of the flask from the last seed stage are used to inoculate the production medium. The inoculated flasks are shaken at a constant temperature for several days, and at the end of the incubation period the contents of the flask are centrifuged or filtered.

For large scale work, it is preferable to conduct the fermentation in suitable tanks provided with an agitator and a means of aerating the fermentation medium. According to this method, the nutrient medium is made up in the tank and sterilized by heating at temperatures of up to about 120° C. Upon cooling, the sterilized medium is inoculated with a previously grown seed of the producing culture, and the fermentation is permitted to proceed for a period of time as, for example, from 1 to 6 days while agitating and/or aerating the nutrient medium and maintaining the temperature at about 24° to 28° C. This method of producing antibiotics $890A_1$ and $890A_3$ is particularly suited for the preparation of large quantities of the antibiotics.

PHYSICAL AND CHEMICAL PROPERTIES OF ANTIBIOTICS $890A_1$ and $890A_3$

PROPERTIES OF ANTIBIOTIC $890A_1$

Antibiotic $890A_1$ is an acidic substance which moves toward the positive pole on electrophoresis at neutral pH.

The sodium salt of antibiotic $890A_1$ is a white powder as lyophilized from aqueous solution, and is very soluble in water.

The ultraviolet absorbance spectrum has a λ-max at 299.5 nm and a λ-min. at 242 nm. The E% at 300 nm of a solution of the sodium salt of antibiotic $890A_1$ in water at neutral pH is 208 for a pure sample; the ratio of absorbance values at 300 nm and 245 nm is 4.25 and the ratio $A_{300}/A_{210}$ is 1.41. More than 92% of the absorption at 300 nm may be eliminated by reaction with hydroxylamine, and a similar decrease is observed upon reaction with cysteine.

The circular dichroism spectrum of $890A_1$ displays a positive maximum at 290.5 nm with a specific ellipticity of 5270 degree-ml. per decimeter-gram, a point of zero ellipticity at 250 nm, and a negative minimum at 214 nm, with specific ellipticity of $-10,910$ degree-ml. per decimeter-gram.

The following table lists the 100 MHz-NMR signals for $890A_1$ sodium salt in $D_2O$ relative to the internal standard, sodium 2,2-dimethyl-2-silapentane-5-sulfonate, hereinafter referred to as DSS; chemical shifts are given in ppm and coupling constants in Hz; the apparent multiplicities are indicated.

1.35 (d, J= 6.5); 198 (s); 3.63 (d of d, J= 5.2 and J= 9.8); ~4.02-4.26 (m); 3.18 (d of d, J= ~11 and J= 10); 3.41 (t, J= 6); 2.97 (d of t, J= 3.5 and J = 6).

The antibiotic potency of $890A_1$, measured on *Vibrio percolans* ATCC 8461, is defined to be 250 units per $HAEA_{300}$ unit.

PROPERTIES OF ANTIBIOTIC $890A_3$

Antibiotic $890A_3$ is an acidic substance which moves to the positive pole on electrophoresis at neutral pH.

The sodium salt is a white powder when lyophilized from aqueous solution.

The ultraviolet absorbance spectrum has a maximum at 300.5 nm and a minimum at 243 nm. The E% at 300 nm of a solution of the sodium salt of antibiotic $890A_3$ in water at neutral pH is 375 for a pure sample; the ratio of absorbances at 300 nm and 245 nm is 3.54. More than 90% of the absorption at 300 nm may be eliminated by reaction with hydroxylamine; and a similar decrease is observed upon reaction with cysteine.

The circular dichroism spectrum of $890A_3$ has a positive maximum at 294 nm with a specific ellipticity of 9127 degrees-ml. per decimeter-gram, a point of zero ellipticity at 249 nm, and a specific ellipticity of $-15,053$ degrees-ml. per decimeter-gram at 220 nm.

The following table lists the 100 MHz-NMR signals for $890A_3$ sodium salt in $D_2O$ relative to the internal standard DSS; chemical shifts are given in ppm and coupling constants in Hz; the apparent multiplicities are indicated.

1.29 (d, J= 6.5); 1.98 (s); 3.42 (d of d, J= 5 and J= 2.4); ~4.01-4.28 (m); 3.14 (d of d, J= 5 and J= 9); 3.39 (t, J= 6.5); 2.92 (d of t, J= ~4 and J= 6).

The antibiotic potency of $890A_3$, measured on *Vibrio percolans* ATCC 8461, is 31 units per $HAEA_{300}$ unit.

Mass Spectral Analysis of $890A_1$ and $890A_3$

The mass spectral data for $890A_1$ annd $890A_3$ are obtained on trimethylsilyl derivatives prepared from ammonium salts of the antibiotics with bis-trimethylsilyl-trifluoro acetamide in dimethyl formamide. Conversions of sodium salts of the antibiotics to the ammonium salts is carried out by using the ammonium salt of an acidic ion exchange resin.

Trimethyl-silylation of $890A_1$ and $890A_3$ results in three different derivatives: a di- and a tri-trimethylsilyl derivative (M.W.s 485 abd 530, respectively) and a small amount of a tetra-trimethylsilyl derivative of a hydrolysed product (M.W. 620) wherein the β-lactam ring is open.

The values of the most important mass spectral fragment are given below:
 di-trimethylsilyl derivative 443.1495; 301.1034; 300.0962; 241,0590 and 86.0610.
 tri-trimethylsilyl derivative: 515.1931; 373.1422 and 158.1000. tetra-trimethylsilyl derivative (only low-resolution signal observed): 620 and 605.

Antibiotics $890A_1$ and $890A_3$ are believed to be isomers having a molecular structure as follows:

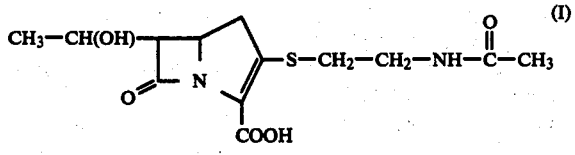

Antibiotics 890A₁ and 890A₃ are further characterized by the following antibiotic spectrum profiles.

The test to determine the antibiotic spectrum profile is carried out by application of a 0.015 ml. droplet on the surface of a 100×15 mm. petri plate containing 5 ml. of seeded nutrient agar and 0.2% yeast extract. The antibiotic 890A₁ is tested at a level of 33 μg/ml. and the antibiotic 890A₃ is tested at a level of 182 μg/ml. The results, expressed in terms of the diameter in millimeters of the zone of inhibition, are set forth in Table III.

TABLE III

*In Vitro* Antibacterial Spectrum
Profile (ASP) of Antibiotics 890A₁ and 890A₃

| Organism | Merck No | ATCC No | Inhib. Zone Diam., mm 890A₁ | 890A₃ |
|---|---|---|---|---|
| Bacillus sp. | MB-633 | — | 40 | 37 |
| Proteus vulgaris | MB-1012 | — | 21 | 24 |
| Pseudomonas aeruginosa | MB-979 | — | 0 | 0 |
| Serratia marcescens | — | 990 | 26 | 28 |
| Staphlococcus aureus | — | 6538 P | 35 | 36 |
| Bacillus subtilis | — | 6633 | 38 | 40 |
| Sarcina lutea | — | 9341 | 38 | 44 |
| Staphylococcus aureus | MB-698 | — | 28 | 34 |
| Streptococcus faecalis | MB-753 | — | 17 | 17 |
| Alcaligenes faecalis | — | 213 | 27 | 34 |
| Brucella bronchiseptica | — | 4617 | 22 | 27 |
| Salmonella gallinarum | MB-1287 | — | 33 | 33 |
| Vibrio percolans | — | 8461 | 34 | 40 |
| Xanthomonas vesicatoria | MB-815 | — | 26 | 26 |
| Proteus vulgaris | — | 21100 | 34 | 34 |
| Escherichia coli | MB-1418 | — | 27 | 32 |
| Pseudomonas stutzeri | — | 11607 | 10 | 32 |
| Klebsiella pneumoniae | MB-1264 | — | 27 | 33 |
| Aerobacter aerogenes | MB-835 | — | 26 | 30 |
| Erwinia atroseptica | — | 4466 | 20 | 30 |
| Pseudomonas aeruginosa | MB-2824 | — | 0 | 32 |
| Corynebacterium pseudoidph. | — | 9742 | 34 | 36 |
| Escherichia coli in synthetic medium | — | 9637 | 27 | 29 |
| Streptococcus faecium | MB-2820 | — | 18 | 24 |
| Streptococcus agalactiae | MB-2875 | — | 36 | 30 |
| Vibrio percolans resistant to ceph. C) | MB-2566 | — | 15 | 34 |
| Proteus vulgaris (episome) | MB-2112 | — | 32 | 38 |
| Proteus mirabilis | MB-3126 | — | 23 | 30 |
| Vibrio percolans +2 × 10⁵ units/ml penicillinase | — | 8461 | 10 | 35 |

Antibiotic 890A₁ exhibits in vivo activity against gram-negative and gram-positive organisms and hence is useful in controlling bacterial infections in animals and humans. In determining the in vivo activity, antibiotic 890A₁ is dissolved in and diluted with 0.15M NaCl, 0.01M sodium phosphate, pH 7.0, to provide five four-fold concentrations of drug for testing. Female white Swiss mice, averaging about 21 g. in weight, were infected intraperitoneally with the test organism suspended in broth. The numbers of organisms injected were determined by standard plate-count techniques. At the time of infection and again 6 hours later, certain of the mice were treated intraperitoneally with the antibiotic. Five mice were used for each concentration of drug tested. An additional two mice, not infected, were treated with the antibiotic to determine whether the amount of agent injected was toxic. Controls of five mice for each of several dilutions of the infecting culture were included in each test in order to calculate the numbers of organisms that were lethal to 50% of the infected, untreated mice (LD₅₀). This calculation was made using survival data of the seventh day after infection, at which time the amount of drug that should protect 50% of the infected mice (ED₅₀) also was calculated.

All animals receiving this challenge and not treated with antibiotic died within 48 hours of the infection. The efficacy of antibiotics 890A₁ having a potency of 5.5 units per μg. against *Salmonella schottmuellari* MB-2837 is set forth below:

| Units/ml.[a] | Route | ED₅₀ × 2 doses Dilution | Units/ml. | μg[b] |
|---|---|---|---|---|
| 908 | ip | 1:32 | 14 | 3 |

[a] 1 unit/ml. = the concentration which produces a 25 mm zone of inhibition against *Vibrio percolans* ATCC 8461.
[b] the μg figure is calculated on the projected purity of 890A₁ at 5500 units/mg.

Antibiotics 890A₁ and 890A₃ are valuable antibiotics active against various gram-positive and gram-negative bacteria and, accordingly, find utility in human and veterinary medicine. The compounds of this invention can be used alone or in combination with each other as antibacterial drugs for treating infections caused by gram-positive or gram-negative bacteria, for example, against *Staphylococcus aureus*, *Proteus mirabilis*, *Escherichia coli*, *Klebsiella pneumoniae* and *Enterobacter cloacae*. The antibacterial materials of the invention may further be utilized as additives to animal feeding-stuffs, for preserving foodstuffs and as disinfectants. For example, they may be employed in aqueous compositions in concentrations ranging from about 0.1 to about 100 parts of antibiotic per million parts of solution or preferably in concentrations ranging from about 1 to about 10 parts of antibiotic per million parts of solution in order to destroy and inhibit the growth of harmful bacteria on medical and dental equipment and as bactericides in industrial applications, for example in water-based paints and in the white water of paper mills to inhibit the growth deleterious bacteria.

The antibiotics of this invention may be used in any one of a variety of pharmaceutical preparations as the sole active ingredients or in combination either with one or more other antibiotics or with one or more pharmacologically active substances. As an example of the former, an aminocyclitol antibiotic such as gentamicin may be coadministered in order to minimize any chance that resistant organisms will emerge. As an example of the latter, diphenoxylate and atropine may be combined in dosage forms intended for the therapy of gastroenteritis. The antibiotics may be employed in capsule form or as tablets, powders or liquid solutions or as suspensions or elixirs. It may be administered orally, topically, intravenously or intramuscularly. Furthermore the antibiotics 890A₁ and 890A₃ may be used in combination with each other.

Tablets and capsules for oral administration may be in unit dose presentation form, and may contain conventional excipients such as binding agents, for example, syrup, acacia, gelatin, sorbitol, tragacanth, or polyvinylpyrrolidone; fillers, for example, lactose, sugar, maize-starch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, syrups, elixirs, etc. or may be presented as a dry product, for reconstitution with water or other suitable vehicles before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminum stearate gel or hydrogenated edible fats; emulsifying agents, for example lecithin, sorbitan monooleate or acacia; nonaqueous vehicles which may include edible oils, for example, almond oil, fractionated coconut oil, oily esters, propylene glycol, or ethyl alcohol; preservatives, for example methyl or propyl p-hydroxybenzoates or sorbic acid. Suppositories will contain conventional suppository bases, e.g. cocoa butter or other glyceride.

Compositions for injection may be presented in unit dose form in ampules, or in multidose containers with an added preservative. The compositions may take such forms as suspensions, solutions, emulsions in oily or aqueous vehicles, and may contain formulatory agents such as suspending, stabilizing and/or dispersing agents. Alternatively, the active ingredient may be in powder form for reconstitution with a suitable vehicle, e.g. sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like.

In veterinary medicine, such as in the treatment of chickens, cows, sheep, pigs and the like, the composition may, for example, be formulated as an intramammary preparation in either long acting or quick-release bases.

The dosage to be administered depends to a large extent upon the condition of the subject being treated, the weight of the host and the type of infection, the route and frequency of administration, the parenteral route being preferred for generalized infections and the oral route for intestinal infections.

In the treatment of bacterial infections in man, the compounds of this invention are administered orally or parenterally, in accordance with conventional procedures for antibiotic administration, in an amount of from about 2 to 600 mg./kg./day and preferably about 5 to 100 mg./kg./day in preferably divided dosage, e.g. three to four times a day. They may be administered in dosage units containing, for example, 25, 330, 400 or 1000 mg. of active ingredient with suitable physiologically acceptable carriers or excipients. The dosage units are in the form of liquid preparations such as solutions or suspensions or as solids in tablets or capsules. It will, of course, be understood that the optimum dose in any given instance will depend upon the type and severity of infection to be treated, and that smaller doses will be employed for pediatric use, all of such adjustments being within the skill of the practitioner in the field.

Included in this invention are the non-toxic, pharmaceutically acceptable salts of $890A_1$ and $890A_3$ for example, the pharmacologically acceptable salts formed with inorganic and organic bases; which include, for example, metal salts derived from alkali metal or alkaline earth metal hydroxides, carbonates or bicarbonates such as those derived from sodium, potassium, ammonium and calcium and salts derived from primary, secondary or tertiary amines such as monoalkylamines, dialkylamines, trialkylamines, lower alkanolamines, di-loweralkanolamines, lower alkylenediamines, N,N-diaralkyl lower alkylenediamines, aralkylamines, amino substituted lower alkanols, N,N-di-lower alkylamino substituted lower alkanols, amino-, polyamino and guanidino-substituted lower alkanoic acids and nitrogen-containing heterocyclic amines. Representative examples include salts derived from sodium hydroxide, ammonium hydroxide, sodium carbonate, sodium bicarbonate, potassium carbonate, potassium hydroxide, calcium carbonate, trimethylamine, triethylamine, piperidine, N-ethylpiperidine, morpholine, quinine, lysine, protamine, arginine, procaine, ethanolamine, morphine, benzylamine, ethylenediamine, N,N'-dibenzylethylenediamine, diethanolamine, piperazine, dimethylaminoethanol, 2-amino-2-methyl-1-propanol, theophylline, N-methylglucamine and the like.

The salts of the compounds of the present invention may be prepared by conventional methods well known in the art. For example, the mono-salts such as monosodium salt obtained by treating one equivalent of sodium hydroxide with one equivalent of the product (I) in a suitable solvent. Also mixed salts with divalent cations may be prepared by combining one mole of a divalent base with one mole of the product (I) plus one equivalent of another acid. Alternatively, salts may be obtained by treating one equivalent of a base having a divalent cation, such as calcium hydroxide, with one equivalent of the product (I). The salts of this invention are pharmacologically acceptable non-toxic derivatives which can be used as the active ingredient in suitable unit-dosage pharmaceutical forms. Also, they may be combined with other drugs to provide compositions having a broad spectrum of activity.

Fermentation broths containing the antibiotics $890A_1$ and $890A_3$ produced in accordance with the procedures described herein have activities ranging from about 2 to 170 units per ml. when assayed in accordance with the disc-diffusion assay using *Vibrio percolans* (ATCC 8461). Antibiotic preparations having at least 5 units per mg. activity of $890A_1$ and $890A_3$ can be purified and the antibiotics recovered by a number of procedures. One such procedure comprises adsorbing the antibiotics $890A_1$ and $890A_3$ on a strongly basic anion exchange resin. Illustrative of such strongly basic anion exchange resins are those having a styrene-divinylbenzene matrix, for example the polystyrene nuclear quaternary ammonium resin Dowex 1 × 2 (manufactured by Dow Chemical Co., Midland, Michigan), on the chloride cycle. Other representative members of this class of strongly basic exchange resins include the following: Duolite A-40, A-42, A-101, A-102 and A-114 (manufactured by Chemical Process Co., Redwood City, California), Amberlite IRA-400, IRA-401 and IRA-410. Alternately, a weekly basic anion exchange resin such as Amberlite IRA-68 may be used. (Amberlite resins are manufactured by Rohm and Haas, Washington Square, Philadelphia 5, Pennsylvania.)

The adsorbed antibiotic is readily eluted from the anion exchange resin with aqueous salt solutions. The eluate so obtained can be further purified, if desired, by other purification procedures. Thus, the eluate can be purified by passing it through a column packed with an acrylic ester polymer of intermediate polarity such as XAD-7 or 8 or through a column packed with a polystyrene, non-polar, hydrophobic crosslinked divinyl benzene polymer such as XAD-1, 2 and 4, preferably XAD-2. (XAD-1, 2, 4, 7, and 8 are manufactured by Rohm and Haas, Washington Square, Philadelphia 5, Pennsylvania). This process partially resolves the antibiotics $890A_1$ and $890A_3$. The fractions rich in $890A_1$ and those rich in $890A_3$ are pooled. These pooled fractions are further purified.

A method of obtaining further purified antibiotic $890A_1$ and $890A_3$ is by the use of gel filtration through polyacrylamide gel having a pore size which excludes molecules having a molecular weight greater than 1800, such as Bio-Gel P-2 (manufactured by Bio.Rad, Richmond, California). Other gels, such as Sephadex G-10 may also be employed for desalting.

The preferred procedure by which antibiotics $890A_1$ and $890_3$ may be obtained in high purity from a broth consists of a centrifugation or filtration to remove solids; an adsorption and elution from an anion-exchange resin such as Dowex-1 $\times$ 2 in the chloride cycle wth NaCl at 3 to 5%, which both concentrations and partially purifies the antibiotic; a passage over a column of suitably prepared XAD-2, retards the antibiotics and thereby purifies and desalts the Dowex-1 $\times$ 2 eluate. Furthermore the antibiotic $890A_3$ is retarded more than the antibiotic $890A_1$ and thereby the two antibiotics are partially resolved. The fractions containing $890A_1$ and $890A_3$ are pooled and further purified. Chromatography on a Dowex-1 $\times$ 2 minus 400 mesh resin, with elution by NaCl and/or $NH_4Cl$, gives a product free from most UV-absorbing impurities (the $NH_4Cl$ is used to provide some buffering capacity in the eluent); and a desalting on Bio-Gel P-2 or Sephadex G-10, removes the salt introduced in the Dowex-1 $\times$ 2 chromatography and further reduces the quantity of other impurities in the antibiotic preparations.

When broths of low potency are treated by the above procedure, the final material may have significant quantities (more than 50%) of extraneous impurities remaining. These impurities may be reduced by an additional cycle of chromatography on Dowex-1 $\times$ 2, minus 400 mesh, with eluation by a solution containing sodium chloride and 50% methanol. It is also advisable, when isolating antibiotic from low-potency broths, to do a second stage of XAD-2 chromatography. This provides additional purification, removes residual salt, and partially resolves the antibiotic $89:A_1$ from $890A_3$. Specifically, the $890A_3$ elutes later than the $890A_1$ and the two may be distinguished by their different ratios of bioactivity to $HAEA_{300}$. Those fractions which demonstrate a ratio of bioactivity on *Vibrio percolans* ATCC 8461 to $HAEA_{300}$ of 250 contain antibiotic $890A_1$ and those fractions which demonstrate a ratio of bioactivity on *Vibrio percolans* ATCC 8461 to $HAEA_{300}$ of 31 contain antibiotic $890A_3$.

Fractions rich in antibiotic $890A_3$ may be treated with penicillinase to remove remaining traces of antibiotic $890A_1$ and further purified by chromatography on Dowex-1 $\times$ 2 and Sephadex G-10.

In laboratory-scale operations (less than 20 liters of sample volume), all chromatography steps except the XAD-2 chromatography are carried out in a cold room at 2°–5° C. The XAD-2 chromatography is carried out at room temperature unless stated otherwise. The pH of antibiotic solutions to be stored is adjusted to 7–8 by careful addition of dilute NaOH or HCl solutions. Aqueous solutions are stored in a refrigerator, or preferably in ice water, and 50% methanol solutions are stored at $-20°$ C.

A flow sheet diagram of the purification procedure for obtaining antibiotics $890A_1$ and $890A_3$ is presented in FIGS. 1 and 2, respectively.

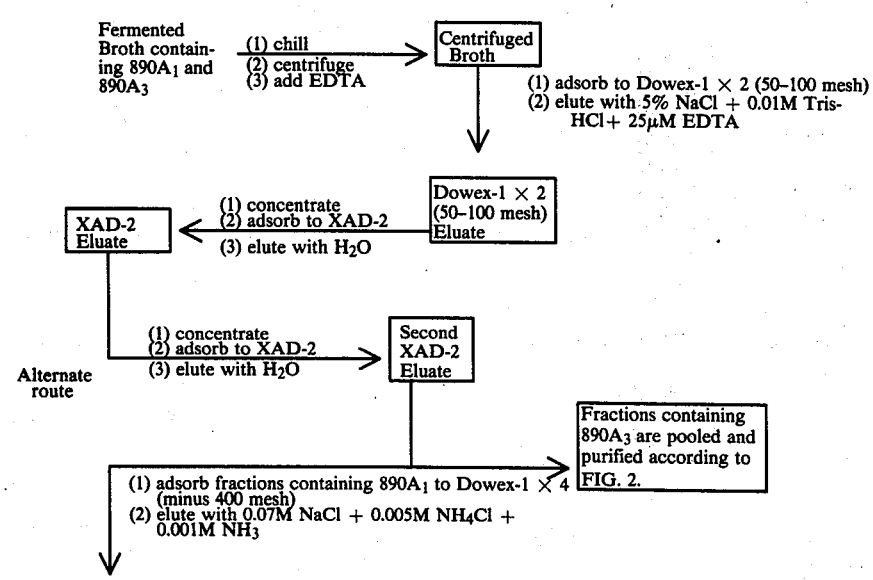

FIG. I

Outline of Purification Process for Antibiotic $890A_1$

FIG. I-continued

Outline of Purification Process for Antibiotic 890A₁

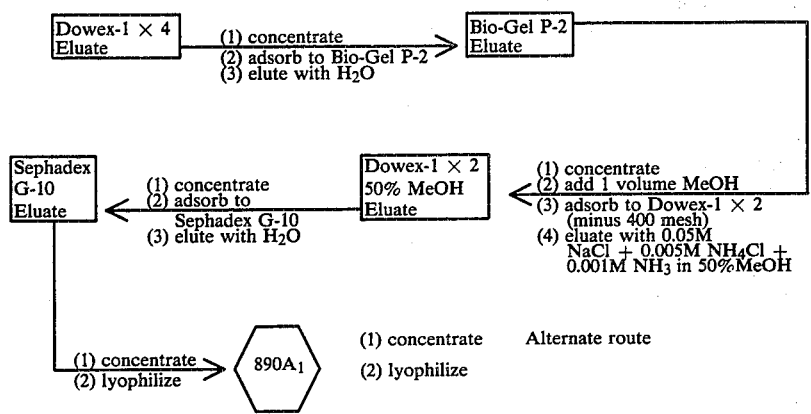

FIG. 2

Outline of Purification Process for Antibiotic 890A₃

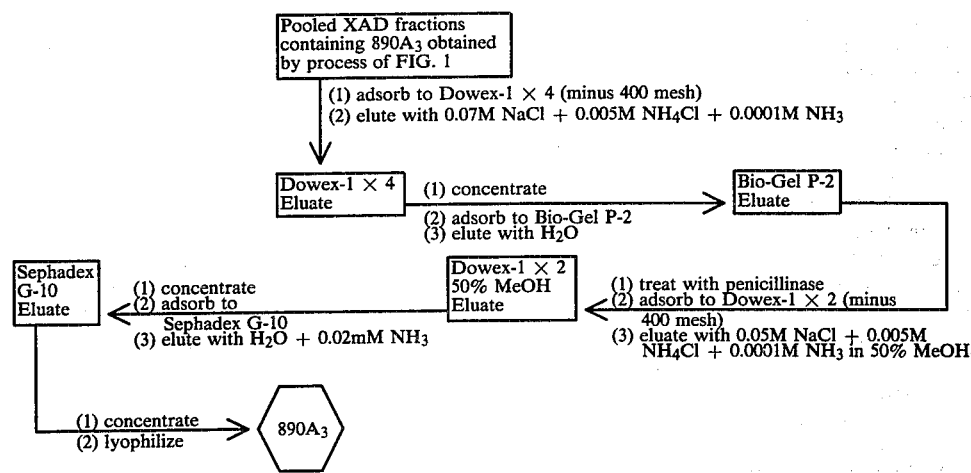

ASSAY PROCEDURES FOR ANTIBIOTICS 890A₁ and 890A₃

1. Bioassay

An agar plate disc-diffusion method is employed using either *Vibrio percolans* ATCC 8461 or *Salmonella gallinarum* MB-1287 as tester organism. A purified sample of antibiotic 890A₁ is used as standard.

Plates containing *Vibrio percolans* ATCC 8461 are prepared as follows:

A lyophilized culture of *Vibrio percolans* ATCC 8461 is suspended in 15 ml. of a sterilized medium containing 8 g./liter of Difco Nutrient Broth and 2 g./liter of yeast extract in distilled water "nutrient broth-yeast extract" (herein after designated NBYE). The culture is incubated overnight on a rotary shaker at 28° C. This culture is used to inoculate the surface of slants containing 1.5% agar in NBYE, and the inoculated slants are incubated overnight at 28° C., and then stored in a refrigerator.

The refrigerated slants prepared from a single lyophilized culture are used for up to four weeks from their preparation, as follows: A loop of inoculum from the slant is dispersed in 50 ml. of NBYE contained in a 250 ml. Erlenmeyer flask. The culture is incubated overnight on a rotary shaker at 28° C. and then diluted to a density giving 50% transmittance at 660 nm. A 33.2 ml. portion of this diluted culture is added to 1 liter of NBYE containing 15 g. of agar and maintained at 46° C. The inoculated agar-containing medium is poured into 100 × 15 mm. plastic petri dishes, 5 ml. per dish, chilled, and maintained at 2°-4° C. for up to 5 days before using.

Plates containing *Salmonella gallinarum* MB-1287 are prepared as follows:

A sealed tube containing *Salmonella gallinarum* MB-1287 cells in skim mil, which had been frozen and lyophilized and sealed under vacuum, is opened and inoculated into 15 ml. of Brain Heart Infusion broth. The cells are allowed to grow without shaking at 37° C. overnight, and the culture is inoculated onto slants of 0.8% BBL Nutrient broth + 0.2% Difco yeast extract + 1.5% agar. After growth overnight at 37° C., a loop of the culture is transferred from the slant to a flask containing 50 ml. of 0.8% nutrient broth + 0.2% yeast extract. The flask is shaken overnight, and 20 ml. of this culture is inoculated into one liter of 0.85 nutrient broth + 0.2% yeast extract + 1.5% agar which had been sterilized and cooled to 48° C. The inoculated NBYE agar is poured immediately into 100 × 5 mm. plastic petri dishes, 5 ml. per dish, and the plates are kept at 0°-3° C. until use.

Filter paper discs of one-half inch diameter are dipped into the solution to be assayed, and are placed on the agar. Alternatively, the discs may be loaded by pipetting one-tenth ml. of solution onto a dry disc, and then placing the disc on the agar. The diameter of the zone of inhibition is measured after appropriate incubation (9–18 hours at 37° C. for *Salmonella gallinarum* MB-1287 or 12–24 hours at 25° C. for *Vibrio percolans* ATCC 8461. If necessary, dilutions of the solutions to be assayed are made in 0.05M potassium phosphate buffer, pH 7.4 "potassium phosphate buffer" (hereinafter referred to as KPB), or in deionized water.

Calculations of potencies proceed as follows: a slope is determined by measuring the zone diameters of a solution of antibiotic $890A_1$ or $890A_3$ and of a four-fold dilution (in KPB) of this solution. Two discs of each concentration are assayed on a single plate, and the average zone size at each concentration is determined. The slope is equal to one-half of the difference of the average zone sizes. Potencies are then calculated by the formula:

Potency (units/ml.) =

$$(\text{Potency of Standard} \times \text{Dilution} \times 10\left(\frac{[D - D_s]\log 2}{\text{slope}}\right)$$

where D is the average diameter of the zones formed by the unknown, $D_s$ is the average diameter of the standard zones, and "Dilution" is the degree to which the unknown was diluted before assay. If no standard is used, $D_s$ is assumed to be 25 mm. and (Potency of Standard) is taken as 1 unit/ml., when measured on *Vibrio percolans* ATTC 8461. Pure $890A_1$ is defined as having a potency of 250 units per hydroxylamine-extinguishable absorbance unit at 300 mm, when used as a standard. Accordingly, the potency of antibiotic $890A_3$ is 31 units per hydroxylamine-extinguishable absorbance unit at 300 mm.

For assays on *Salmonella gallinarum* MB-1287 plates, a slope is determined in the same way as on *Vibrio percolans* ATCC 8461 plates. When no standard is used, only relative potencies are calculated. If no slope is measured, a value of 2.3 mm. is assumed. The potency calculation proceed as with the *Vibrio percolans* ATTC 8461 assay. If no $890A_1$ standard is used, a control of penicillin G at 250 μg/ml. may be employed in order to verify that the sensitivity of the organisms is in the normal range.

II. Assay Procedure for Determining "890 Assay Units"

The conventional disc-plate assay procedure is employed and the discs are ½ inch in diameter. The routinely poured 10 ml./plate inoculated with *Vibrio percolans* (ATCC 8461) is used and the standard is cephaloridine. Four concentrations of cephaloridine constitute the standard — 3.12, 6.25, 12.5 and 25 mcg per ml. with the 12.5 mcg per ml. as a reference solution. The zone diameters on a 5 ml. plate for the standard are as follows:

| Conc. (mcg/ml.) | Zone Diameter (mm.) |
|---|---|
| 3.12 | 16.8 |
| 6.25 | 22.3 |
| 12.5 | 25.0 |
| 25 | 29.6 |

A unit is defined as the amount of antibiotic-producing a 25 mm. zone of inhibition on a 5 ml. plate. Therefore, in this assay a concentration of 12.5 mcg per ml. of cephaloridine is considered equivalent to 1 unit of 890A. Since the slope of the line for cephaloridine is 4.0 calculations of the potency of a sample are made using a slope of 4.0.

III. Hydroxylamine Reaction Both antibiotics $890A_1$ and $890A_3$ react with hydroxylamine and produce a substance with greatly diminished absorbance at 300 mm. This provides the basis for a quantitative assay of the antibiotics $890A_1$ and $890A_3$.

The solution to be assayed is brought to 0.05M in potassium phosphate, pH 7.4 by adding 1/20th volume of a solution containing 0.8M $K_2HPO_4$ and 0.2M $KH_2PO_4$. Then one-hundredth volume of 1M hydroxylamine hydrochloride is added, and the absorbance at 300 nm is measured at intervals of one-half to two minutes. The reaction is conducted at 22°–28° C. First-order kinetics are assumed and a half-life is estimated from the absorbance decrease during the first ten minutes. From this half-life, the time is estimated beyond which no further absorbance decrease should be observed and observations are continued beyond that time. If no further decrease is observed beyond that time, the total absorbance of the hydroxylamine) is taken as the "Hydroxylamine-extinguishable absorbance at 300 nm ($HAEA_{300}$)." If absorbance decrease is observed beyond that time, the rate of background absorbance decrease is calculated, and the observed decrease at that time is corrected for background decrease, assuming that background decrease is linear with time. The corrected value is then recorded as the $HAEA_{300}$.

The number of $HAEA_{300}$ units is equal to the $HAEA_{300}$ multiplied by the volume in ml. The examples which follow illustrate the methods by which the products of this invention may be obtained. However, the examples are illustrative only and it should be apparent to one having ordinary skill in the art that this invention includes the functionally equivalent products and methods for their preparation. Therefore, any modification of the processes described herein which results in the formation of an identical product should be construed as constituting an analogous method. The described processes are capable of wide variation and modification and any minor departure or extension is considered as being within the skill of the artisan and as falling within the scope of this invention.

EXAMPLE 1

Shake Flask Production of Mixture Containing Antibiotics $890A_1$ and $890A_3$

A portion of a slant culture of *Streptomyces flavogriseus* MA-4434a is used to inoculate a 250 ml. baffled Erlenmeyer seed flask containing 50 ml. medium A having the following composition:

| Medium A | |
|---|---|
| Dextrose | 10.0 g. |
| Yeast Autolysate (+Ardamine) Type pH) | 10.0 g. |
| $MgSO_4 \cdot 7H_2O$ | 0.05 g. |
| *Phosphate buffer | 2.0 ml. |
| Distilled $H_2O$ | 1000 ml. |
| pH 6.5 | |

-continued

| +Ardamine: Yeast Products Corporation | |
|---|---|
| *Phosphate Buffer solution | |
| KH$_2$PO$_4$ | 91.0 g. |
| Na$_2$HPO$_4$ | 95.0 g. |
| Distilled H$_2$O | 1000 ml. |

This seed flask is shaken at 28° C. on a 220 rpm shaker (2" throw) for 2 days when growth is satisfactory.

Three 250 ml. Erlenmeyer flasks, each containing 40 ml. of Medium B having the following composition:

| Medium B | |
|---|---|
| Tomato paste | 20.0 g. |
| Whole oats (ground) | 20.0 g. |
| Distilled H$_2$O | 1000 ml. |
| pH: adjust to 7.0 using NaOH | | are inoculated with 2 ml. (5%) per flask of the growth from the seed flask. These 3 production flasks are shaken at 28° C. on a 220 rpm shaker (2" throw) for up to 4 days. At 3 days the supernatent from centrifuged broth gives a 22 mm. zone of inhibition against *Proteus vulgaris,* MB838 and 15 mm. zone against *Salmonella gallinarum,* MB1287 using ¼ inch assay discs on standard assay plates.

EXAMPLE 2

Shake Flask Production of Mixture Containing Antiobiotics 890A$_1$ and 890A$_3$

A portion of a slant culture of *Streptomyces flavogriseus* MA-4434a is used to inoculate a 250 ml. baffled Erlenmeyer seed flask containing 50 ml. medium A having the following composition:

| Medium A | |
|---|---|
| Dextrose | 10.0 g. |
| Yeast Autolysate (+Ardamine Type pH) | 10.0 g. |
| MgSO$_4$ . 7H$_2$O | 0.05 g. |
| *Phosphate buffer | 2.0 ml. |
| Distilled H$_2$O | 1000 ml. |
| pH 6.5 | |
| +Ardamine: Yeast Products Corporation | |
| *Phosphate Buffer solution | |
| KH$_2$PO$_4$ | 91.0 g. |
| Na$_2$HPO$_4$ | 95.0 g. |
| Distilled H$_2$O | 1000 ml. |

This seed flask is shaken at 28° C. on a 220 rpm shaker (2" throw) for 1 day when growth is satisfactory. It is held at 4° C. for two days until used.

Three 2000 ml. Erlenmeyer flasks, each containing 200 ml. of Medium B having the following composition:

| Medium B | |
|---|---|
| Tomato paste | 20.0 g. |
| Whole oats (ground) | 20.0 g. |
| Distilled H$_2$O | 1000 ml. |
| pH: adjust to 7.0 using NaOH | | are inoculated with 7 ml. per flask (3.5%) of the growth from the seed flask. These 3 production flasks are shaken at 28° C. on a 220 rpm shaker (2" throw) for 4 days.

Assays, run on centrifuged aliquots using ½" discs on standard assay plates, and the pH values are as follows:

| Age | *V. percolans* ATCC 8461 | *S. gallinarum* MB 1287 | pH |
|---|---|---|---|
| 3 day | 22 mm. | 16 mm. | 6.1 |
| 4 day | 26 mm. | 18 mm. | 7.5 |

EXAMPLE 3

Shake Flask Production of Mixture Containing Antiobiotics 890A$_1$ and 890A$_3$

A tube of lyophilized culture of *Streptomyces flavogriseus* MA-4434a is opened aseptically and the contents suspended in a tube containing 0.8 ml. sterile Davis salts solution having the following composition:

| Davis Salts | |
|---|---|
| Sodium citrate | 0.5 g. |
| K$_2$HPO$_4$ | 7.0 g. |
| KH$_2$PO$_4$ | 3.0 g. |
| (NH$_4$)$_2$SO$_4$ | 1.0 g. |
| MgSO$_4$ . 7H$_2$O | 0.1 g. |
| Distilled H$_2$O | 1000 ml. |

This suspension is used to inoculate slants and plates of various media. A natural isolate is selected from one of these plates and streaked onto a slant of medium A having the following composition:

| Medium A | |
|---|---|
| Dextrose | 10.0 g. |
| Peptone | 5.0 g. |
| Yeast Extract | 3.0 g. |
| NaCl | 12.705 g. |
| KCl | 0.72 g. |
| FeSO$_4$(NH$_4$)$_2$SO$_4$ . 6H$_2$O | 0.0351 g. |
| MgCl$_2$ . 6H$_2$O | 5.32 g. |
| CaCl$_2$ . 2H$_2$O | 0.728 g. |
| Distilled H$_2$O | 1000 ml. |
| pH 7.4 (before sterilization) | |
| Agar | 25.0 g. |

This inoculated slant is incubated for 7 days and after sporulation a spore suspension is made with 0.8 ml. of sterile Davis salts. Four second generation slants of Medium A are inoculated from this suspension. The inoculated slants are incubated for one week at 28° C. and then stored at 4°–6° C. until used 14 days later. A one-half portion of the surface growth of one of these second generation slants is used to inoculate baffled 250 ml. Erlenmeyer flasks containing 50 ml. of medium B. having the following composition:

| Medium B | |
|---|---|
| Yeast Autolysate (+Ardamine) | 10.0 g. |
| Glucose | 10.0 g. |
| Phosphate Buffer* | 2.0 ml. |
| MgSO$_4$ . 7H$_2$O | 50 mg. |
| Distilled H$_2$O | 1000 ml. |
| pH: adjust to 6.5 using HCl or NaOH | |

+Ardamine: Yeast Products Corporation

-continued

| *Phosphate Buffer solution | |
|---|---|
| $KH_2PO_4$ | 91.0 g. |
| $Na_2HPO_4$ | 95.0 g. |
| Distilled $H_2O$ | 1000 ml. |

Three seed flasks are inoculated to provide sufficient inoculum for the 12 two liter production flasks fermented in this batch. The seed flasks are shaken for one day at 28° C. on a 220 rpm shaker (2" throw). The flasks are removed from the shaker and stored for one day at 4° C. The contents of these seed flasks are used to inoculate 12 two liter unbaffled Erlenmeyer production flasks (8 ml. of inoculum per flask) containing 250 ml. of the production medium C having the following composition:

| Medium C | |
|---|---|
| Tomato Paste | 20.0 g. |
| Whole Ground Oats | 20.0 g. |
| Distilled $H_2O$ | 1000 ml. |
| pH adjusted to 7.0 using NaOH | |

After inoculation, production flasks are incubated at 28° C., with agitation on a 220 rpm shaker (2" throw) for four days. At the end of this period, flasks are harvested and assayed for activity by using standard *Salmonella gallinarium* MB1287 and *Vibrio percolans* ATCC 8461 assay plates, using ½ inch assay discs dipped into centrifuged broth samples.

| Assay at Harvest | |
|---|---|
| Harvest Age (hours) | 96 |
| pH | 7.4 |
| *Salmonella gallinarum* (mm. zone) | 23 |
| *Vibrio percolans* ATCC 8461 (mm. zone) | 29 |

The fermentation broth is filtered and the pH of the filtrate adjusted from 7.7 to 7.0 with dilute HCl. The pH adjusted filtrate, 2.65 l., is adsorbed on 135 ml. of IRA68 resin in the chloride cycle (a weekly basic cross-linked acrylic polymer anion exchange resin manufactured by Rohm and Haas Co., Washington Square, Philadelphia 5, Pennsylvania.) at 20 ml./min. collecting the spent as one fraction. The adsorbate is washed with 250 ml. of water and eluted with 5% NaCl collecting 6 × 100 ml. fractions. All fractions are assayed against *Vibrio percolans*, ATCC 8461 and *Salmonella gallinarum*, MB1287, usng the disc-plate method. These assays indicated that eluate fractions 1 through 3 contain 45% of the bioactivity applied to the resin.

Eluate fractions 1 through 3 are combined to yield 310 ml. of solution. To this solution is added 15 g. of sodium chloride and the solution cooled to 2° C. The cold solution is adjusted to pH 3.0 with HCl and immediately extracted with 150 ml. of n-butyl alcohol. The extraction is repeated with two additional 150 ml. portions of n-butyl alcohol. The n-butyl alcohol phases are back-extracted in serial fashion with 3 × 75 ml. portions of water. During the extraction the aqueous phases are maintained at pH 7 by the addition of dilute sodium hydroxide. All fractions are assayed against *Vibrio percolans*, ATCC 8461 and *Salmonella gallinarum*, MB-1287 and the results are tabulated below as percent of starting bioactivity:

| Fraction | | Recovery |
|---|---|---|
| Feed | | 100% |
| Spent Aqueous | | 12% |
| Spent n-butyl alcohol | No. 1 | 0 |
| | No. 2 | 0 |
| | No. 3 | 0 |
| Aqueous back-extract | No. 1 | 25% |
| | No. 2 | 37% |
| | No. 3 | 5% |

The first and second back-extracts are freeze-dried individually. The freeze-dried solids are combined to yield 984 mg. of product.

EXAMPLE 4

Production of Mixture Containing Antibiotic $890A_1$ and $890A_3$

A tube of lyophilized culture of *Streptomyces flavigriseus* MA-4434a is opened aseptically and the contents suspended in a tube containing 0.8 ml. sterile Davis salts solution having the following composition:

| Davis Salts | |
|---|---|
| Sodium citrate | 0.5 g. |
| $K_2HPO_4$ | 7.0 g. |
| $KH_2PO_4$ | 3.0 g. |
| $(NH_4)_2SO_4$ | 1.0 g. |
| $MgSO_4 \cdot 7H_2O$ | 0.1 g. |
| Distilled $H_2O$ | 1000 ml. |

This suspension is used to inoculate 4 slants of medium a having the following composition:

| Medium A | |
|---|---|
| Dextrose | 10.0 g. |
| Peptone | 5.0 g. |
| Yeast Extract | 3.0 g. |
| NaCl | 12.705 g. |
| KCl | 0.72 g. |
| $FeSO_4(NH_4)_2SO_4 \cdot 6H_2O$ | 0.0351 g. |
| $MgCl_2 \cdot 6H_2O$ | 5.32 g. |
| $CaCl_2 \cdot 2H_2O$ | 0.728 g. |
| Distilled $H_2O$ | 1000 ml. |
| pH 7.4 (before sterilization) | |
| Agar | 25.0 g. |

The inoculated slants are incubated for one week at 27°–28° C. and then stored at 4°–6° C. until used 10 days later. A one-half portion of the surface growth of one of these slants is used to inoculate baffled 250 ml. Erlenmeyer flasks containing 50 ml. of medium B having the following composition:

| Medium B | |
|---|---|
| Yeast Autolysate (+Ardamine) | 10.0 g. |
| Glucose | 10.0 g. |
| Phosphate Buffer* | 2.0 ml. |
| $MgSO_4 \cdot 7H_2O$ | 50 mg. |
| Distilled $H_2O$ | 1000 ml. |
| pH: adjust to 6.5 using HCl or NaOH | |
| +Ardamine: Yeast Products Corporation | |
| *Phosphate Buffer solution | |
| $KH_{KH2}PO_4$ | 91.0 g. |
| $Na_2HPO_4$ | 95.0 g. |
| Distilled $H_2O$ | 1000 ml. |

Three seed flasks are inoculated to provide sufficient inoculum for the 12 two liter production flasks fermented in this batch. The seed flasks are shaken for one day at 28° C. on a 220 rpm shaker (2" throw). The flasks are removed from the shaker and stored for one day at 4° C. The contents of these seed flasks are used to inoculate 12 two liter unbaffled Erlenmeyer production flasks (7 ml. of inoculum per flask) containing 250 ml. of the production medium C having the following composition:

| Medium C | |
|---|---|
| Tomato Paste | 20.0 g. |
| Primary Yeast | 10.0 g. |
| Dextrin (Amidex) | 20.0 g. |
| Deionized H$_2$O | 1000 ml. |
| pH adjust to 7.3 using NaOH | |

After inoculation, production flasks are incubated at 24° C. with agitation on a 220 rpm shaker (2" throw) for four days and five hours. At the end of this period flasks are harvested and assayed for activity by using standard *Salmonella gallinarum* MB1287 and *Vibrio percolans* ATCC 8461 assay plates using ½ inch assay discs dipped into centrifuged broth samples. The results are tabulated below:

| Assay at Harvest | |
|---|---|
| Harvest age (hours) | 101 |
| pH | 7.1 |
| *Salmonella callinarum* (mm. zone) | 31 |
| *Vibrio percolans* (mm. zone) | 43 |

The fermentation broth is centrifuged. To the clear centrifugate, 2.2 l., at pH 6.8, is added 22 mg. of (ethylenedinitrilo)tetraacetic acid and the pH adjusted to 7.2. The pH adjusted centrifugate is adsorbed on 150 ml. of Dowex 1 × 2 resin in the Cl$^-$ cycle at 15 ml./min. collecting the spent stream as one fraction. The adsorbate is washed with 150 ml. of deionized water containing 10 μg./ml. of (ethylenedinitrilo) tetraacetic acid and eluted with 5% NaCl containing 10 μg./ml. of (ethylenedinitrilo) tetraacetic acid collecting 5 × 75 ml. fractions. All fractions are assayed against *Vibrio percolans*, ATCC 8461 and the results are tabulated below as percent of starting bioactivity:

| Fraction | Recovery |
|---|---|
| Feed | 100% |
| Spent | 0 |
| 5% NaCl eluates fractions 2 to 4 | 75% |
| water displacement wash | 1% |

Fifty ml. of fraction 3 of the 5% NaCl eluate is adjusted to pH 5.2 with dilute HCl and percolated through a 100 ml. column of XAD-2 which has been washed with five column volumes of 60% aqueous acetone (v/v), five column volumes of deionized water and five column volumes of 5% (w/v) NaCl solution containing 25μM neutral EDTA in deionized water, and washed with 5 columm volumes of deionized water. The resin is developed with deionized water containing 10 μg./ml. of (ethylenedinitrilo) tetraacetic acid collecting 2 × 25 ml. and 5 × 10 ml. fractions checking the effluent until negative to acidic silver nitrate. A negative silver nitrate response is obtained at the end of the fifth 10 ml. fraction. Development with deionized water is continued until 4 × 100 ml. fractions have been collected. The resin is developed with 60% acetone water containing 4 μg./ml of (ethylenedinitrilo) tetraacetic acid until 2 × 50 ml. fractions are collected. All fractions are assayed against *Vibrio percolans*, ATCC 8461 and the results are tabulated below:

| Sample Feed | Volume 50 ml. | Recovery 100% |
|---|---|---|
| Fraction 1 | 25 | 0 |
| 2 | 25 | 0 |
| 3 | 10 | 0 |
| 4 | 10 | 0 |
| 5 | 10 | 1 |
| 6 | 10 | 4.5 |
| 7 | 10 | 7 |
| 8 | 100 | 60 |
| 9 | 100 | 6 |
| 10 | 100 | 1 |
| 11 | 100 | 0 |
| 12 | 50 | 1 |
| 13 | 50 | 0 |

Fraction eight is concentrated to 10 ml. and freeze-dried to yield 34.2 mg. of solids.

A 33.2 mg. portion of the freeze-dried solids is taken up in 1.5 ml. of 1% n-butyl alcohol water and applied on a column of Bio-Gel P-2 (200–400 mesh) 1.4 × 81.5 cm. which had previously been equilibrated with 1% n-butyl alcohol in water. The gel is developed with the same solvent at 1 ml./min., collecting 2 ml. fractions. Every fraction 29 through 46, is assayed against *Vibrio percolans* ATCC 8461. A bioactivity peak in fractions 36 through 44, having a maximum in fraction 39, is observed. Fractions 38 through 41 are combined and freeze-dried to yield 4.0 mg. of antibiotic.

EXAMPLE 5

Shake Flask Production of Mixture Containing Antibiotics 890A$_1$ and 890A$_3$

A tube of lyophilized culture of *Streptomyces flavogriseus* MA-4434a is opened aseptically and the contents suspended in a tube containing 0.8 ml. of sterile Davis salts having the following composition:

| Davis salts | |
|---|---|
| Sodium citrate | 0.5 g. |
| K$_2$HPO$_4$ | 7.0 g. |
| KH$_2$PO$_4$ | 3.0 g. |
| (NH$_4$)$_2$SO$_4$ | 1.0 g. |
| MgSO$_4$ . 7H$_2$O | 0.1 g. |
| Distilled H$_2$O | 1000 ml. |

This suspension is used to inoculate four slants of medium A having the following composition:

| Medium A | |
|---|---|
| Glycerol | 20.0 g. |
| Primary Yeast | 5.0 g. |
| Fish Meal | 15.0 g. |
| Distilled H$_2$O | 1000 ml. |
| Agar | 20.0 g. | pH: adjust to 7.2 using NaOH

The inoculated slants are incubated for one week at 27°–28° C. and then stored at 4°–6° C. until used.

A one-third portion of the surface growth from two slants is used to inoculate 6 baffled 250 ml. Erlenmeyer flasks containing 50 ml. medium B having the following composition:

| Medium B | |
|---|---|
| Yeast Autolysate (+Ardamine) | 10.0 g. |
| Glucose | 10.0 g. |
| Phosphate Buffer* | 2.0 ml |
| MgSO$_4$ . 7H$_2$O | 50 mg. |
| Distilled H$_2$O | 1000 ml. | pH: adjust to 6.5 using HCl or NaOH
+Ardamine: Yeast Products Corporation

| *Phosphate Buffer solution | |
|---|---|
| KH$_2$PO$_4$ | 91.0 g. |
| Na$_2$HPO$_4$ | 95.0 g. |
| Distilled H$_2$O | 1000 ml. |

The seed flask is shaken for one day at 27°–28° C. on a 220 rpm shaker (2" throw). The flask and contents are stored stationary for one day at 4° C.

Twenty two 2 liter Erlenmeyer production flasks, each containing 300 ml. of Medium C, are inoculated with 8 ml. per flask of the growth from the seed flask. The medium C has the following composition:

| Medium C | |
|---|---|
| Tomato Paste | 20.0 g. |
| Primary Yeast | 10.0 g. |
| Dextrin (Amidex) | 20.0 g. |
| CoCl$_2$ . 6H$_2$O | 5.0 mg. |
| Distilled H$_2$O | 1000 ml. | pH: adjust to 7.2–7.4 using NaOH

After inoculation, the production flasks are incubated at 24° C., with agitation on a 212 rpm shaker (2" throw), for four days and five hours. The flasks are harvested and assayed for activity by using standard *Salmonella gallinarum* MA1287 and *Vibrio percolans* ATCC 8461 assay plates using ¼ inch assay discs dipped into centrifuged broth samples. Samples are diluted with 0.02M phosphate buffer, pH 7.0 when necessary. The results are tabulated below:

| Harvest Age hours | 101 |
|---|---|
| pH | 7.1 |
| *Salmonella gallinarum* (mm. zone) | 31 |
| *Vibrio percolans* 1/10 dil (mm. zone) | 24.5 |
| 890 Assay Units | 46 |

Four liters of whole fermentation broth, containing 23 units/ml. is chilled to 3° C. and centrifuged in 200 ml. portions at 9000 rpm for 15 minutes each. To the combined supernatants (3.6 liters) is added 1 ml. of 0.1M neutral EDTA and 10 ml. of 1M Tris-HCl buffer, pH 7.5. The solution of 0.10M neutral EDTA is prepared by dissolving 0.1 mole of disodium ethylenediamine tetraacetic acid in 1 liter deionized water and bringing the pH to 7 by addition of sodium hydroxide.

The centrifuged broth is adsorbed on a column of Dowex-1 × 2 (cl$^-$), 50–100 mesh, 5.1 cm. ×20 cm. bed dimensions, which had been washed with 1 liter of deionized water prior to application of the centrifuged broth. The flow rate during application is 50–80 ml. per minute. When application is complete, the column is washed with 500 ml. of deionized water containing 25μM neutral EDTA, and then eluted with 1300 ml. of 5% NaCl in deionized water containing 25μM neutral EDTA. Nine fractions are collected, counting from the first application of NaCl solution. Fractions 1 through 4 contain 100 to 115 ml. per fraction and fractions 5 through 9 contain 170 to 185 ml. per fraction. The fractions are assayed for bioactivity on *Salmonella gallinarum* MB1287 plates. Bioactivity appears in fractions 2 through 9 with a peak at fractions 4 and 5.

The ultraviolet absorption of appropriate dilutions of each fraction is measured in a Gilford Model 2000 spectrophotometer, and the ratio of bioactivity to absorbance at 220 nm ($A_{220}$) is calculated for each fraction. Those fractions with biopotency/$A_{220}$ ratios greater than one-half the maximum value are pooled for further processing. Thus fractions 4 through 7 are pooled, containing 30% of the applied bioactivity.

The pooled NaCl eluate is concentrated to 100 ml. under reduced pressure while maintaining the temperature below 35° C. during evaporation.

The pH of the concentrate is adjusted to 5.2 by addition of 3 ml. of 1 molar HCl, and the concentrate applied on a column of XAD-2 (3.5 cm. wide and 57 cm. long) which had been washed with 3 liters of 60% aqueous acetone (v/v), 3 liters of deionized water, 3 liters of 5% (w/v) NaCl solution containing 25μM neutral EDTA in deionized water, and 1 liter of saturated sodium chloride. After the washing, the column is transferred to a cold room maintained at 3° C., before the concentrate is applied.

The applied concentrate is drained to bed level, and the active fractions eluted with 1.3 liters of 25μM neutral EDTA in deionized water. Fractions of 10 ml. each are collected, counting from the first application of concentrate to the column.

Every fifth fraction is assayed for bioactivity on *Salmonella gallinarum* MB1287 plates, and the $A_{220}$ values are measured using appropriate dilutions. Those fractions with biopotency/$A_{220}$ ratios greater than one-half the maximum value are combined. Thus fractions 48 to 95 are pooled, containing 50% of the applied activity, which represents 17% of the activity of the filtered broth.

The pooled XAD-2 fractions are concentrated to 50 ml. and applied on a column of Dowex-1 × 4 (Cl$^-$), minus 400 mesh, with resin bed dimensions 1.3 × 13 cm. The column is rinsed with 15 ml. of deionized water and eluted with 400 ml. of 0.08M NaCl plus 0.005M NH$_4$Cl plus 0.0001M NH$_3$ in deionized water. Fractions of 10 ml. each are collected at a flow rate of 0.6 ml. per minute. Activity equivalent to 100% of the applied activity is eluted in fractions 23 to 30, with the peak of activity in fraction 26. Fractions 26 and 27 have the highest ratios of absorbance at 300 nm to absorbance at 220 nm ($A_{300}/A_{220}$), and these two are pooled for desalting. The total activity in 26 and 27 is 7390 units, or 59% of the applied activity. To the pooled fractions 26 and 27 is added 5 μl. of 0.01M neutral EDTA.

The pooled fractions are concentrated by rotary evaporation under reduced pressure to 1.95 ml., and the concentrate is applied to a column of Bio-Gel P-2, 200 to 400 mesh, with bed dimensions of 2.2 × 80 cm. The sample is washed in with rinses of 1 ml. and 2 ml. of deionized water, and then eluted with deionized water at a flow rate of 0.7 ml. per minute. Fractions of 2.1 to 2.2 ml. are collected. The main peak of UV absorbance is found in tubes 89 to 100, containing 74% of the applied absorbance units, measured at 300 nm ($A_{300}$ units). Fractions 92 through 98 are pooled, concentrated to 2 ml., and lyophilized to give product. This sample contains 18.6 $A_{300}$ units, representing 5.8% of the bioactivity contained in the starting broth. Fractions 89 to 91 and 99 to 100 are further purified as set forth in Example 6.

EXAMPLE 6

Shake Flask Production of Antibiotic 890A$_1$

A tube of lyophilized culture of Streptomyces flavogriseus MA-4434a is opened aseptically and the contents suspended in a tube containing 0.8 ml. of sterile Davis salts having the following composition:

| Davis salts | |
|---|---|
| Sodium citrate | 0.5 g. |
| K$_2$HPO$_4$ | 7.0 g. |
| KH$_2$PO$_4$ | 3.0 g. |
| (NH$_4$)$_2$SO$_4$ | 1.0 g. |
| MgSO$_4$ . 7H$_2$O | 0.1 g. |
| Distilled H$_2$O | 1000 ml. |

This suspension is used to inoculate four slants of medium A having the following composition:

| Medium A | |
|---|---|
| Glycerol | 20.0 g. |
| Primary Yeast | 5.0 g. |
| Fish Meal | 15.0 g. |
| Distilled H$_2$O | 1000 ml. |
| Agar | 20.0 g. | pH: adjust to 7.2 using NaOH

The inoculated slants are incubated for one week at 27°–28° C. and then stored at 4°–6° C. until used.

A one-third portion of the growth from three slants is used to inoculate 9 baffled 250 ml. Erlenmeyer flask containing 50 ml. medium B having the following composition:

| Medium B | |
|---|---|
| Yeast Autolysate (+Ardamine) | 10.0 g. |
| Glucose | 10.0 g. |
| Phosphate Buffer* | 2.0 ml |
| MgSO$_4$ . 7H$_2$O | 50 mg. |
| Distilled H$_2$O | 1000 ml. | pH: adjust to 6.5 using HCl or NaOH
+Ardamine: Yeast Products Corporation

| *Phosphate Buffer solution | |
|---|---|
| KH$_2$PO$_4$ | 91.0 g. |
| Na$_2$HPO$_4$ | 95.0 g. |
| Distilled H$_2$O | 1000 ml. |

The seed flask is shaken for one day at 27°–28° C. on a 220 rpm shaker (2" throw). The flask and contents are stored stationary for one day at 4° C.

Thirty three 2 liter Erlenmeyer production flasks, each containing 250 ml. of Medium C, are inoculated with 8 ml. per flask of the growth from the seed flask. The medium C has the following composition:

| Medium C | |
|---|---|
| Tomato Paste | 20.0 g. |
| Primary Yeast | 10.0 g. |
| Dextrin (Amidex) | 20.0 g. |
| CoCl$_2$ . 6H$_2$O | 5.0 mg. |
| Distilled H$_2$O | 1000 ml. | pH: adjust to 7.2–7.4 using NaOH

After inoculation, the production flasks are incubated at 24° C., with agitation on a 212 rpm shaker (2" throw), for four days. The flasks are harvested and assayed for activity by using standard Salmonella gallinarum MB1287 and Vibrio percolans ATCC 8461 assay plates using ½ inch assay discs dipped into centrifuged broth samples. Samples are diluted with 0.02M phosphate buffer, pH 7.0 when necessary. The reults are tabulated below:

| Harvest Age hours | 96 |
|---|---|
| pH | 7.2 |
| Salmonella gallinarum (mm. zone) | 29.5 |
| Vibrio percolans 1/10 dil (mm. zone) | 31 |
| 890 Assay Units | 40 |

Seven liters of whole fermentation broth is chilled to 3° C. and centrifuged in 200 ml. portions at 9000 rpm for 15 minutes each.

To the combined supernatants is added 7 ml. of 0.1M neutral EDTA, and the entire sample is adsorbed on a Dowex-1 × 2 (Cl$^-$), 50-100 mesh column, bed dimensions 5.1 × 25 cm., at a flow rate of 40 ml. per minute. The column is washed with 500 ml. of deionized water containing 5 ml. of 1M Tris-HCl buffer, pH 7.0, and 25μM neutral EDTA. The antibiotic is eluted with 1 liter of deionized water containing 50 g. of sodium chloride, and the column is then washed with 300 ml. of deionized water. Fractions of 100 ml. are collected, starting from the first appearance of salt at the column outlet. Bioactivity appears in fractions 1 through 10 with a peak at fraction 2. The fractions with the highest ratios of biopotency/$A_{220}$ are combined. Thus, fractions 2 through 5 containing 17% of the applied activity, are pooled.

The pooled fractions are concentrated to 110 ml. by rotary evaporation under reduced pressure, and the pH is adjusted to 5.8 by addition of 4.2 ml. of 1M HCl. The adjusted concentrate is applied on a column of XAD-2, bed dimensions 3.8 by 50 cm., which had been previously washed with 3 liters of 60% aqueous acetone (v/v), followed by 3 liters of deionized water, 3 liters of 5% (w/v) sodium chloride, and 1 liter of 25% (w/v) sodium chloride in deionized water. The applied concentrate is allowed to drain to bed level. The antibiotic is eluted with deionized water at a flow rate of 15 ml./minute. Twenty-two fractions of 100 ml. each are collected, counting from the first application of sample. Bioactivity appears in fractions 6 through 22, with a peak at fractions 9 and 10. Fractions with biopotency/$A_{220}$ ratios greater than 0.3 times the peak value are pooled. Thus fractions 9 through 20 are combined for further processing. To these fractions are added fractions 89, 90, 91, 99 and 100 from the Bio-Gel P-2 column of Example 5. The combined pool is concentrated to 70 ml. by rotary evaporation under reduced pressure.

The concentrate is adsorbed on a Dowex-1 × 4 (Cl$^-$) minus 400 mesh column with bed dimensions 2.2 × 27 cm. The column is washed with 50 ml. of deionized water, and the antibiotic eluted with 2 liters of 0.070M NaCl + 0.005M NH$_4$Cl + 0.0001M NH$_3$ in deionized water at a flow rate of 2 ml. per minute. Fractions of 9.5 ml. are collected.

The main peak of antibiotic is eluted in fractions 142 to 163. Fractions 146 through 157 contained material with the highest $A_{300}/A_{250}$ ratios and these were combined for further processing.

The combined fractions 146–157 are concentrated to 3 ml. by rotary evaporation under reduced pressure, and the concentrate is brought to pH 6.5 by addition of 5 μl. of 1M NH$_3$. The concentrate is applied on a column (2.2 × 70 cm.) of Bio-Gel P-2 (200-400 mesh), which had been washed with 20 ml. of 5M NaCl and 500 ml. of deionized water. After the concentrate has drained to bed level, two rinses of 1 ml. each of deionized water are applied and allowed to drain to bed level. The column is then eluted with deionized water at a flow rate of 0.6 ml. per minute. Fractions of 2.9 ml. are collected.

The main peak of antibiotic is eluted in fractions 63 to 70. Fractions 64 and 65 have the highest $A_{300}/A_{250}$ ratios, and are pooled for further workup. These two fractions contain 44% of the UV absorption at 300 nm which has been applied to the Bio-Gel P-2 column.

The combined fractions 64 and 65 are rotary evaporated under reduced pressure to 2 ml., and then shell frozen and lyophilized in a 14 ml. screw-cap vial for 8 hours to give 2.25 mg. substantially pure antibiotic 890A$_1$ (45.5 A$_{300}$ units).

EXAMPLE 7

Shake Flask Production of Antibiotic 890A$_3$

A tube of lyophilized culture of *Streptomyces flavogriseus* MA-443a is opened aseptically and the contents suspended in a tube containing 0.8 ml. of sterile Davis salts having the following composition:

| Davis salts | |
|---|---|
| Sodium citrate | 0.5 g. |
| K$_2$HPO$_4$ | 7.0 g. |
| KH$_2$PO$_4$ | 3.0 g. |
| (NH$_4$)$_2$SO$_4$ | 1.0 g. |
| MgSO$_4$ . 7H$_2$O | 0.1 g. |
| Distilled H$_2$O | 1000 ml. |

This suspension is used to inoculate four slants of medium A having the following composition:

| Medium A | |
|---|---|
| Glycerol | 20.0 g. |
| Primary Yeast | 5.0 g. |
| Fish Meal | 15.0 g. |
| Distilled H$_2$O | 1000 ml. |
| Agar | 20.0 g. | pH: adjust to 7.2 using NaOH

The inoculated slants are incubated for one week at 27°–28° C. and then stored at 4°–6° C. until used (not longer than 21 days).

A one-third portion of the growth from four slants is used to inoculate 12 baffled 250 ml. Erlenmeyer flask containing 50 ml. medium B having the following composition:

| Medium B | |
|---|---|
| Yeast Autolysate ($^+$Ardamine) | 10.0 g. |
| Glucose | 10.0 g. |
| Phosphate Buffer* | 2.0 ml |
| MgSO$_4$ . 7H$_2$O | 50 mg. |
| Distilled H$_2$O | 1000 ml. | pH: adjust to 6.5 using HCl or NaOH
+Ardamine: Yeast Products Corporation

| -continued | |
|---|---|
| Medium B | |
| *Phosphate Buffer solution | |
| KH$_2$PO$_4$ | 91.0 g. |
| Na$_2$HPO$_4$ | 95.0 g. |
| Distilled H$_2$O | 1000 ml. |

The seed flask is shaken for one day at 27°–28° C. on a 220 rpm shaker (2" throw). The flask and contents are stored stationary for one day at 4° C.

Forth-four 2 liter Erlenmeyer production flasks, each containing 200 ml. of Medium C., are inoculated with 8 ml. per flask of the growth from the seed flask. The medium C has the following composition:

| Medium C | |
|---|---|
| Tomato Paste | 20.0 g. |
| Primary Yeast | 10.0 g. |
| Dextrin (Amidex) | 20.0 g. |
| CoCl$_2$ . 6H$_2$O | 5.0 mg. |
| Distilled H$_2$O | 1000 ml. | pH: adjust to 7.2–7.4 using NaOH

After inoculation, the production flasks are incubated at 24° C., with agitation on a 212 rpm shaker (2" throw), for four days and five hours. The flasks are harvested and assayed for activity by using standard *Salmonella gallinarum* MB1287 and *Vibro percolans* ATCC 8461 assay plates using ¼ inch assay discs dipped into centrifuged broth samples. Samples are diluted with 0.02M phosphate buffer, pH 7.0 when necessary. The results are tabulated below:

| Harvest Age hours | 101 |
|---|---|
| pH | 7.2 |
| *Salmonella gallinarum* | |
| (mm. zone) | 35 |
| *Vibrio percolans* 1/10 dil | |
| (mm. zone) | 34 |
| 890 Assay Units | 121 |

The total of 7.0 liters of whole broth obtained from this fermentation is chilled to 3° C. and centrifuged in 200 ml. portions at 9000 rpm for 15 minutes each. To the combined supernatant is added 1.7 ml. of 0.1M neutral EDTA and the batch is held at 3° C.

The above fermentation is repeated under identical conditions with the exception that the 44 two liter Erlenmeyer production flasks are inoculated with 7 ml. per flask with growth from the seed flask. The pH and assay results are tabulated below:

| Harvest Age hours | 101 |
|---|---|
| pH | 7.3 |
| *Salmonella gallinarum* | |
| (mm. zone) | 38 |
| *Vibrio percolans* 1/10 dil | |
| (mm. zone) | 39 |
| 890 Assay Units | 92.8 |

The total of 7.4 liters of whole broth obtained from this fermentation is chilled to 3° C. and centrifuged in 200 ml. portions at 9000 rpm for 15 minutes each. To the combined supernatant is added 1.8 ml. of 0.1M neutral EDTA.

The supernatant from the centrifuged broth resulting from the two above fermentations in this Example are combined to give a total volume of 13 liters and a potency of 80 units/ml. by assay on *Vibrio percolans* ATCC 8461.

The combined supernatant is passed through a column of Dowex-1 × 2 (Cl$^-$), 50-100 mesh, with bed dimensions 4.7 cm. × 50 cm., at a flow rate of 60 ml. per minute. The column is washed with 1 liter of deionized water, and the antibiotic is eluted with 5 liters of 5% (w/v) NaCl solution containing 0.01M Tris-HCl buffer, pH 7.0, and 25μM neutral EDTA. Fractions of 220 ml. are collected at a flow rate of 50 ml. per minute, and the fractions are assayed on *Salmonella gallinarum* MB1287 plates.

Antibiotic activity appears in fractions 3 through 26, with a peak at fractions 5 and 6. Fractions 5 through 9, having the highest ratios of biopotency/$A_{220}$, are combined for further processing. The pH of the pooled fractions is 7.8, and the pooled fractions contain 24% of the initial bioactivity, as measured on *Salmonella gallinarum* MB1287 plates.

The combined fractions 5 through 9 are concentrated to 150 ml. by rotary evaporation under reduced pressure, and applied to a column (4.9 cm. × 47 cm. bed dimensions) of XAD-2 which had been washed with 5 liters of 60% (v/v) aqueous acetone followed by 5 liters of deionized water, and 5 liters of 50 g./liter NaCl in deionized water. The sample is applied in 20 ml. portions, draining the column to bed level each time. When application is complete, three 20 ml. portions of deionized water are applied and drained to bed level each time. The sample is eluted with deionized water at a flow rate of 20 ml. per minute. All operations involving the XAD column are carried out at room temperature (24° C.), and the fractions which are eluted are chilled rapidly in an ice bath immediately after collection. Fractions of 95 to 230 ml. are collected.

Antibiotic activity appears in fractions 2 through 21, as measured by assay on *Salmonella gallinarum* MB1287 plates, with a peak at fractions 5 through 7 (being 510 to 895 ml. of eluted volume, counting from the first application of deionized water). Fractions 6 through 21 are pooled, having ratios of biopotency/$A_{220}$ within 50% of the observed peak value. The total bioactivity recovered is 280,000 units, which is 112% of the apparent applied activity.

The pooled fractions 6 through 21 are concentrated to 68 ml. by rotary evaporation under reduced pressure, and then diluted to 112 ml. by addition of deionized water. The concentrate is applied on a column (2.2 cm. × 21 cm. bed dimensions) of Dowex-1 × 4 (Cl$^-$) minus 400 mesh. The column is washed with 20 ml. of deionized water, and the antibiotics are eluted with 2 liters of 0.07M NaCl + 0.005M NH$_4$Cl + 0.0001M NH$_3$ in deionized water, at a flow rate of 1.6 ml. per minute. Fractions of 8 ml. each are collected.

The main peak of absorbance at 300 nm appears in fractions 153 through 182, with a maximum at fraction 162. Fractions 157 through 179, having the highest ratios of absorbance at 300 nm to absorbance at 245 nm., are combined for further processing. The combined fractions have a total of 780 absorption units at 300 nm.

These pooled fractions are concentrated by rotary evaporation under reduced pressure to 7 ml., and the pH adjusted to 7.5 by addition of 20 μl. of 1M NaOH. The solution is concentrated further to 5 ml., and applied on a column (2.2 × 75 cm.) of Bio-Gel P-2, 200-400 mesh. The sample is washed into the column bed with two rinses of 1 ml. each of deionized water, and eluted with deionized water at a flow rate of 0.6 ml. per minute. Ten fractions of 3.3 ml. followed by sixty fractions of 2.65 ml. and ten fractions of 2.0 ml. are collected.

The main peak of absorbance at 300 nm appears in fractions 60 through 68. The pH values of the peak fractions are adjusted in the range 7.5 to 8.0 by addition of from 1.5 to 2.5 μl. of 0.1M NaOH. Fractions 62, 63, 64 and 65 are frozen and lyophilized individually in 14 ml. glass vials, and stored at $-20°$ C. under vacuum. These four fractions contain a total of 606 absorption units at 300 nm.

In order to isolate antibiotic 890A$_3$ free from 890A$_1$, advantage is taken of the relatively higher resistance of antibiotic 890A$_3$ to degradation by penicillinase, as follows:

Bio-Gel fraction 63 is combined with fractions 61, 66 and 67 from the Bio-Gel column. These four combined fractions have a total of 235 absorbance units at 300 nm. To this is added 0.2 ml. of 1M Tris-HCl buffer, ph 7.5, and 0.2 ml. of penicillinase [Difco "Bacto-Penase," containing 500,000 units per ml. (1000 LU/ml.) wherein the term LU refers to Levy units; 1,000 LU will inactivate 500,000 units of penicillin G].

After 113 minutes at 23° C., an additional 0.2 ml. of penicillinase is added. After an additional 7 hours at room temperature, another 0.2 ml. of penicillinase is added, and after an additional two hours at room temperature, the reaction mixture is chilled in an ice bath. The terminated reaction mixture is diluted to 15 ml. by addition of 5 ml. of deionized water. The absorbance of the diluted reacted preparation is 6.3 at 300 nm of which 2.64 is extinguishable by reaction with cysteine.

The reaction mixture is adsorbed on a Dowex-1 × 4 (Cl$^-$) minus 400 mesh column, bed dimensions 2.15 × 40 cm. The antibiotic 890A$_3$ is eluted with 0.07M NaCl + 0.005M NH$_4$Cl + 0.0001M NH$_3$ in deionized water, at a flow rate of 3 ml. per minute. Fractions of 13.8 ml. each are collected.

The main peak of absorbance at 300 nm appears in fractions 185 through 203. Fractions 187 through 200 have the highest $A_{300}/A_{245}$ ratios and are combined for further processing. The combined fractions have a total of 31 $A_{300}$ units.

The combined fractions are concentrated to 4 ml. by rotary evaporation under reduced pressure, and the concentrate is applied on a column (2.2 × 70 cm.) of Bio-Gel P-2, 200-400 mesh. The antibiotic 890A$_3$ is eluted with deionized water at a flow rate of 0.6 ml. per minute. Thirty fractions of 3.3 ml. followed by fifty fractions of 2.65 ml. are collected.

The main peak of absorbance at 300 nm appears in fractions 64 through 74, with a maximum at fraction 70. Fractions 66 through 70 are combined, containing 19 $A_{300}$ units, or 61% of the applied units. The pooled samples are concentrated to 1.5 ml. by rotary evaporation under reduced pressure, and the concentrate frozen and lyophilized to give 5.4 mg. of solids containing the antibiotic 890A$_3$ plus residual salts.

EXAMPLE 8

Preparation of Antibiotics 890A$_1$ and 890A$_3$

A tube of lyophilized culture of *Streptomyces flavogriseus* MA-4434a is opened aseptically and the contents suspended in a tube containing 0.8 ml. of sterile Davis salts having the following composition:

| Davis salts | |
|---|---|
| Sodium citrate | 0.5 g. |
| $K_2HPO_4$ | 7.0 g. |
| $KH_2PO_4$ | 3.0 g. |
| $(NH_4)_2SO_4$ | 1.0 g. |
| $MgSO_4 \cdot 7H_2O$ | 0.1 g. |
| Distilled $H_2O$ | 1000 ml. |

This suspension is used to inoculate four slants of medium A having the following composition:

| Medium A | |
|---|---|
| Glycerol | 20.0 g. |
| Primary Yeast | 5.0 g. |
| Fish Meal | 15.0 g. |
| Distilled $H_2O$ | 1000 ml. |
| Agar | 20.0 g. | pH: adjust to 7.2 using NaOH

The inoculated slants are incubated for one week at 27°–28° C. and then stored at 4°–6° C. until used (not longer than 21 days).

Ten ml. of medium B having the composition:

| Medium B | |
|---|---|
| Yeast Autolysate (+Ardamine) | 10.0 g. |
| Glucose | 10.0 g. |
| Phosphate Buffer* | 2.0 ml |
| $MgSO_4 \cdot 7H_2O$ | 50 mg. |
| Distilled $H_2O$ | 1000 ml. | pH: adjust to 6.5 using HCl or NaOH
+Ardamine: Yeast Products Corporation

| *Phosphate Buffer solution | |
|---|---|
| $KH_2PO_4$ | 91.0 g. |
| $Na_2HPO_4$ | 95.0 g. |
| Distilled $H_2O$ | 1000 ml. | is transferred aseptically to one of these slants, the spores and aerial mycelia scraped into suspension, and 3.3 ml. of this suspension used to inoculate a 2 liter baffled Erlenmeyer flask containing 500 ml. of Medium B. This seed flask is shaken at 28° C. on a 160 rpm shaker (2" throw) for 36 hours at which time the growth is satisfactory.

The growth from this seed flask is used to inoculate a 189 liter stainless steel seed tank containing 160 liters of Medium B. This tank is operated at 28° C. using an agitation rate of 150 rpm and an airflow of 3 cu. ft. per minute for 24 hours. Defoamer, Polyglycol 2000 (Dow Chemical Corp.), is used as required but not to exceed 0.1%. pH determinations are made as follows:

| Age, Hours | 0 | 12 |
|---|---|---|
| pH | 6.3 | 6.35 |

Forty-three liters of the growth in this seed tank is used to inoculate a 756 liter stainless steel fermentor containing 467 liters of Medium C, wherein Medium C has the composition:

| Medium C | |
|---|---|
| Tomato Paste | 20.0 g. |
| Primary Yeast | 10.0 g. |
| Dextrin (Amidex) | 20.0 g. |
| $CoCl_2 \cdot 6H_2O$ | 5.0 mg. |

-continued

| Medium C | |
|---|---|
| Distilled $H_2O$ | 1000 ml. | pH: adjust to 7.2–7.4 using NaOH

This tank is run at 25° C. using an agitation rate of 146 rpm and an airflow of 9 cm. ft. per minute for 92 hours. Additional defoamer, Polyglycol 2000, is added as required, not to exceed 0.1%. Antibacterial assays are run on *Salmonella gallinarum* MB1287, *Vibrio percolans* ATCC 8461 and the data is as follows:

| Age Hrs. | 0 | 12 | 24 | 36 | 48 | 60 | 72 | 84 | 92 |
|---|---|---|---|---|---|---|---|---|---|
| pH | 6.6 | 6.7 | 6.65 | 6.3 | 6.0 | 6.4 | 6.15 | 6.5 | 6.5 |
| MB-1287 mm. | — | — | — | S | — | 19 | 26 | 28 | 32 |
| ATCC 8461 mm. (1–10) | — | — | — | S | — | 21 | 24 | 26 | 30 |
| 890A units/ml. | | | | NA | NA | 6.8 | 13.5 | 24.9 | 24.3 |

The 890A units/ml. are determined as set forth in the section with the heading "II. Assay Procedure for Determining '890 Assay Units'."

one hundred twenty-five gallons of broth is chilled to 5° C. and centrifuged through a Titan P-9 centrifuge. Fifty pounds of Celite is added to the 100 gallons of supernatant, and the suspension filtered through a Shriver 18-inch filter press. The 91 gallons of filtrate is absorbed on a column containing seven gallons of Dowex-1 × 2 ($Cl^-$), 50–100 mesh, and the column washed with 10 gallons of deionized water. The mixture of antibiotics $890A_1$ and $890A_3$ is eluted with thirty gallons of 5% NaCl + 0.01M Tris HCl buffer, pH 7.0 + 25μM neutral EDTA in deionized water. Fractions of 5 gallons each are collected. The mixture of antibiotics $890A_1$ and $890A_3$ appears in fractions 3 through 6, with peak potency in fractions 4 and 5. Fractions 4, 5, and 6, containing 8% of the activity of the filtered broth, are combined and concentrated under reduced pressure to 2 gallons.

The two gallons of concentrate are applied to a column containing 10 gallons of XAD-2 which had been previously washed with 50 gallons of 60% aqueous acetone followed by 50 gallons of deionized water and 50 gallons of 5% NaCl solution. The concentrate is eluted with 37.5 gallons of deionized water. Three fractions of 2.5 gallons followed by six fractions of five gallons are collected. The activity appears in fractions 1 through 6, with a peak of potency in fraction 3. Fractions 4 and 5, containing 64% of the activity applied to the XAD column, or 370,000 units are pooled.

Fractions 4 and 5 are concentrated to 120 ml. by evaporation under reduced pressure. The pH is adjusted to 6.5 and the concentrate is applied to a column (7 × 50 cm.) of XAD-2 which had been washed with 8 liters of 60% aqueous acetone followed by 4 liters of deionized water and 8 liters of 5% NaCl in deionized water. The sample is drained to bed level and the column rinsed with three 20 ml. portions of deionized water, draining to bed level each time. The antibiotic is then eluted with seven liters of deionized water at a flow rate of 40 ml. per minute. Eight fractions of 200 ml. followed by fourteen fractions of 400 ml. are collected. Antibiotic activity appears in fractions 4 through 19, containing 77% of the bioactivity applied on the column (as measured by the *Salmonella gallinarum* MB1287 assay), with a peak of activity in fractions 6 through 8.

The ratio of bioactivity of the fractions on *Vibrio percolans* ATCC 8461 and the $HAEA_{300}$ for the fractions is determined. Those fractions displaying the rato value of about 250 indicate the presence of antibiotic $890A_1$ and those having a ratio of about 31 indicate the presence of antibiotic $890A_3$. Accordingly, fraction 7, 8 and 9, containing mostly antibiotic $890A_1$, are combined and further processed as set forth below under the heading a) *Purification of Antibiotic* $890A_1$. Fractions 10, 11, 12 and 13, containing mostly antibiotic $890A_3$, are combined and further processed as set forth below under the heading b) *Purification of Antibiotic* $890A_3$.

(a) Purification of Antibiotic $890A_1$

The combined fractions 7, 8 and 9 from the second XAD-2 column containing 480 hydroxylamine-extinguishable absorbance units at 300 nm are concentrated to 100 ml. under reduced pressure. The sample is applied on a column of Dowex-1 × 4 ($Cl^-$) minus 400 mesh resin, bed dimensions 2.15 × 40 cm., and eluted with 4 liters of 0.075M $NH_4Cl$ + 0.001M $NH_3$ is deionized water. Fractions of 12 ml. each are collected at a flow rate of 2 ml. per minute.

The antibiotic activity, as judged by assay on *Salmonella gallinarum* MB1287, appears in fractions 119 through 146, with a peak in fractions 134 through 140. The ultraviolet absorbances at 300 nm, 245 nm and 220 nm are measured for every third fraction in the region of bioactivity, and the hydroxylamine-extinguishable absorbance at 300 nm is measured for several fractions on either side of the peak. Fractions 129 through 141, which have the highest ratios of hydroxylamine-extinguishable 300 nm absorbance to UV absorbance at 200 nm, are combined.

The combined fractions 129 through 141 are concentrated to 4 ml. and 0.1 ml. of 1M $NH_3$ is added. The concentrate is applied to a column of Bio-Gel P-2, 200–400 mesh, with bed dimensions 2.2 × 70 cm., and eluted with deionized water at a flow rate of 1 ml. per minute. Fractions of 3.1 ml. each are collected.

The main peak of UV absorbance at 300 nm appears in fractions 40 through 47. Fractions 42, 43 and 44 have the highest ratios of hydroxylamine-extinguishable 300 nm absorbance to UV absorbance at 220 nm, and these are combined. These combined fractions contain a total of 207 absorbance units at 300 nm, of which 133.4 are hydroxylamine-extinguishable, representing a recovery of 44% of the applied hydroxylamine-extinguishable absorbance.

The combined Bio-Gel P-2 fractions are diluted with an equal volume of methanol and applied on a column of Dowex-1 × 2 ($Cl^-$) minus 400 mesh, bed dimensions 2.15 cm. × 40 cm., which had been pre-equilibrated with 50% (v/v) methanol. The antibiotic is eluted with 2 liters of 0.065M $NH_4Cl$ + 0.001M $NH_3$ in 50% methanol at a flow rate of 2 ml. per minute. Fractions of 12.5 ml. are collected.

The main peak of absorbance at 300 nm appears in fractions 59 through 72. Fractions 62 through 68 have the highest $A_{300}/A_{245}$ ratios, and are combined. The combined fractions contain 93.7 absorbance units at 300 nm, of which 76.3 are hydroxylamine-extinguishable. This represents a recovery of 57% of the applied hydroxylamine-extinguishable absorption, in the peak fractions.

These pooled fractions are concentrated to 3.4 ml. by rotary evaporation under reduced pressure, and 100 μl. of 1M $NH_3$ is added. The adjusted concentrate is applied on a column (2.15 cm. × 70 cm.) of Sephadex G-10 which had been previously washed with 20 ml. of saturated NaCl solution and 20 ml. of 12% $NH_4Cl$ and then with 500 ml. of deionized water. The sample is eluted with deionized water at a flow rate of 2.15 ml. per minute. Four fractions of 10.3 ml. followed by 56 fractions of 3.23 ml. are collected. The first peak of ultraviolet-absorpton at 300 nm, containing the desalted antibiotic $890A_1$ appears in fractions 25 through 47. Fractions 28 through 41 are combined and the pH is found to be 3.5. The pH is adjusted to 7.3 by addition of 8 μl. of 1M $NH_3$. The pooled fractions contain 28 absorption units at 300 nm of which 18 are hydroxylamine-extinguishable.

Two ml. of these combined fractions are removed for reference and the remainder concentrated to 2.0 ml. The pH of the concentrate is adjusted to 7.4 by addition of 0.7 μl. of 1M $NH_3$.

Fifty microliters of the concentrate is removed and the remainder is frozen and lyophilized in a 14 ml. glass vial to give 4.32 mg. of solids containing the antibiotic $890A_1$ plus residual salts.

(b) Purification of Antibiotic $890A_3$

Combined fractions 10 through 13 obtained from the second XAD-2 column are concentrated to 40 ml. and applied on a column (2.15 cm. × 40 cm. bed dimensions) of Dowex-1 × 4 ($Cl^-$) minus 400 mesh. The antibiotic is eluted with three liters of 0.075M $NH_4Cl$ and 0.001M $NH_3$ in deionized water, at a flow rate of 3 ml. per minute. Fractions of 9 ml. are collected. Antibiotic activity, assayed by *Vibrio percolans* ATCC 8461, appears in fractions 165 through 234, with a peak of activity in fractions 195 through 201.

Fractions 186 through 213 are combined, containing a total of 472 $A_{300}$ units, of which 312 were extinguishable by reaction with hydroxylamine.

These combined fractions are concentrated to 4.2 ml. by rotary evaporation under reduced pressure. The concentrate is applied to a column of Bio-Gel P-2 (200–400 mesh) with bed dimensions 2.15 × 60 cm. The sample is allowed to drain to bed level, and two rinses of 1 ml. each of deionized water are applied and drained to bed level. The column is eluted with deionized water at a flow rate of 1 ml. per minute, collecting fractions of 2.6 ml. each.

The antibiotic $890A_3$ eluted in fractions 38 through 48, with a peak at fraction 41, determined by hydroxylamine-extinguishable absorbance at 300 nm. Fractions 40 through 43 are pooled, containing 260 $A_{300}$ units, of which 173 are hydroxylamine-extinguishable.

To remove residual contamination of antibiotic $890A_3$ by antibiotic $890A_1$, the combined desalted fractions 40 through 43 are treated with 50 μl. of penicillanase [Difco "Bacto-Penase" containing 500,000 units per ml. (1000 LU/ml. wherein the term LU refers to Levy units; 1,000 LU will inactivate 500,000 units of penicillin G)] and 0.1 ml. of 1M Tris-HCl buffer, pH 7.5. The reaction is allowed to stand at 23° C. for 6 hours, and then 3 ml. of deionized water and 15 ml. of methanol is added. This mixture is applied on a column (2.15 × 44 cm. bed dimensions) of Dowex-1 × 2 ($Cl^-$) minus 400 mesh, which had been packed in 50% methanol and washed with two liters of 50% (v/v) methanol. The antibiotic 890A$_3$ is eluted with 2 liters of 0.05M NaCl + 0.005M NH$_4$Cl + 0.0001M NH$_3$ in 50% methanol. Fractions of 9.2 ml. are collected. The main peak of UV absorbance, measured at 300 nm, occurs in fractions 74 through 88. Fractions 78 through 85 are pooled. The total absorbance units at 300 nm in these fractions, after removal of the methanol by evaporation under reduced pressure, is 97.6, of which 87.5 are extinguishable by reaction with hydroxylamine.

The pooled fractions 70 through 85 are concentrated to 3.92 ml. by rotary evaporation under reduced pressure, and the concentrate applied on a column of Sephadex G-10 (2.15 × 70 cm. bed dimensions) which had been washed with 4 ml. of 4M NH$_3$, followed by equilibration with 0.15mM NH$_3$ in deionized water. After two washes of 1 ml. each of 0.02mM NH$_3$, the antibiotic 890A$_3$ is eluted with 0.02mM NH$_3$, at a flow rate of 0.8 ml. per minute. Forty-nine fractions of 2.45 ml., followed by twenty fractions of 3.33 ml. are collected. The main peak of absorbance at 300 nm appears in fractions 35 through 53. Fractions 38 through 46, having the highest A$_{300}$/A$_{245}$ values, are combined for further processing. The combined fraction have a total of 65 absorbance units at 300 nm. The pooled fractions are rotary evaporated under reduced pressure to 2.84 ml., and divided into two equal portions which are quick-frozen and lyophilized separately in 14 ml. glass vials to give antibiotic 890A$_3$. One sample contains 32.0 A$_{300}$ units in 0.88 mg., and the other contains 31.9 A$_{300}$ units in 0.82 mg. The former sample containing 32.0 A$_{300}$ units was subjected to NMR analysis and showed the following peaks:

1.29 (d, J= 6.5); 1.98 (s); 3.42 (d of d, J= 5 and J= 2.4); ~4.02–4.28 (m); 3.14 (d of d, J= 5 *Shake and* J= 9); 3.39 (t, J= 6.5); 2.92 (d of t, J= ~4 and J = 6).

The above table lists the 100 MHz-NMR signals for 890A$_3$ sodium salt in D$_2$O relative to the internal standard DSS; chemical shifts are given in ppm and coupling constants in Hz; apparent multiplicities are indicated.

EXAMPLE 9

Shake Flask Production of Antibiotic 890A$_1$

A tube of lyophilized culture of *Streptomyces flavogriseus MA*-4600a is aseptically opened and the contents suspended in a tube containing 1.5 ml. of sterile medium A having the following composition:

| Medium A | |
|---|---|
| Yeast Extract | 10.0 g. |
| Glucose | 10.0 g. |
| MgSO$_4$ . 7H$_2$O | 0.05 g. |
| *Phosphate Buffer | 2 ml. |
| Distilled H$_2$O | 1000 ml. |

| *Phosphate Buffer solution | |
|---|---|
| KH$_2$PO$_4$ | 91.0 g. |
| Na$_2$HPO$_4$ | 95.0 g. |
| Distilled H$_2$O | 1000 ml. |

This suspension is used to inoculate a 250 ml. triple-baffled Erlenmeyer seed flask containing 54 ml. of seed medium B having the following composition:

| Medium B | |
|---|---|
| Autolyzed Yeast (Ardamine+) | 10.0 g. |
| Glucose | 10.0 g. |

| Medium B —continued | |
|---|---|
| MgSO$_4$ . 7H$_2$O | 0.05 g. |
| Phosphate Buffer | 2 ml. |
| Distilled H$_2$O | 1000 ml. | pH: adjust to 6.5 with NaOH
+Ardamine: Yeast Products Corporation

| *Phosphate Buffer solution | |
|---|---|
| KH$_2$PO$_4$ | 91.0 g. |
| Na$_2$HPO$_4$ | 95.0 g. |
| Distilled H$_2$O | 1000 ml. |

The seed flask is stoppered with cotton and shaken for 30 hours at 28° C. ± 1° C. on a 220 rpm gyrotory shaker (2" throw).

Fifty 250 ml. unbaffled Erlenmeyer production flasks, each containing 40 ml. of production of medium C are inoculated with 1 ml. per flask of the broth from the seed flask. The production flasks are stoppered with cotton.

| Medium C | |
|---|---|
| Tomato paste | 20.0 g. |
| Primary yeast | 10.0 g. |
| Dextrin (Amidex) | 20.0 g. |
| CoCl$_2$ . 6H$_2$O | 5.0 mg. |
| Distilled H$_2$O | 1000 ml. | pH: adjust to 7.2–7.4 with NaOH

After inoculation, the production flasks are incubated at 28° C. ± 1° C. with shaking on a 220 rpm gyrotory shaker (2" throw) for 3 days. The flasks are assayed for activity against standard *Vibrio percolans* ATCC 8461 assay plates using ¼ assay discs dipped into centrifuged fermentation broth samples. Samples are diluted with 0.05M phosphate buffer, pH 7.4. The results are tabulated below:

| Harvest Age hours | 72 |
|---|---|
| pH | 6.4 |
| *Vibrio percolans* | |
| (1/100 Dilution) Assay | 23 mm. |
| 890 Assay, units/ml. | 103 |

The 890A units/ml. are determined as set forth in the section with the heading "II. Assay Procedure for Determining '890 Assay Units'."

The whole broth is centrifuged in 200 ml. portions in polycarbonate bottles at 9000 rpm for 15 minutes to give 1600 ml. of combined supernatants with a potency of 104 units/ml. To this is added 0.5 ml. of neutral EDTA.

The centrifuged broth is adsorbed on a Dowex-1 × 2 (Cl$^-$), 50–100 mesh column, bed dimensions 3.8 × 22 cm., at a flow rate of 6 to 20 ml./min. The column is rinsed with 100 ml. of deionized water and eluted with 1 liter of deionized water containing 50 g. of sodium chloride, 0.02M Tris HCl buffer, pH 7.0, and 25 μM neutral EDTA, at a flow rate of 6 ml./min. Fractions of 10 ml. are collected.

Antibiotic 890A$_1$ appears in fractions 13 through 81, with a maximum at fractions 25 to 33, counting from the first application of salt eluate. Fractions 24 through 41, having the highest biopotency/A$_{220}$ ratios, are combined for further processing. The combined fractions have a total of 29,000 units, or 17% of the applied bioactivity.

The Dowex eluate is concentrated to 10 ml., the pH is adjusted to 6.5 with dilute hydrochloric acid, and the concentrate is applied on a column of XAD-2, bed dimensions 3.3 × 36 cm., which had been previously washed with 2 liters each of 60% aqueous acetone, deionized water, and 5% (w/v) sodium chloride in deionized water. The sample is eluted with deionized water at a flow rate of 6 ml./min. Fractions of 40 to 260 ml. are collected.

Antibiotic activity appears in fractions 6 through 14, extending from 220 to 2560 ml. of eluted volume. The peak is at fractions 9 and 10, extending from 370 to 590 ml. of eluted volume. Fractions 9 through 12, extending from 370 to 1060 ml. of eluted volume, have the highest ratios of $HAEA_{300}/A_{220}$, and are combined for further processing. These fractions have 36,600 units, equal to 126% of the apparent applied activity.

The combined fractions 9 through 12 are concentrated to 100 ml. and the concentrate applied on a column of Dowex-1 × 4 ($Cl^-$), minus 400 mesh, bed dimensions 2.2 × 41 cm., at a flow rate of 2 ml./min. The column is rinsed with 50 ml. of deionized water, and eluted with 3 liters of 0.07M NaCl + 0.005M $NH_4Cl$ + 0.0001M $NH_3$ in deionized water, at a rate of 2 ml./min. Fractions of 10.8 ml. are collected, starting from the first application of eluent.

The main peak of antibiotic $890A_1$ appears in fractions 181 through 217, with a maximum at fraction 198. Fractions 186 through 210, containing a total of 114 absorption units at 300 nm., are pooled.

The pooled fractions are concentrated to 4.0 ml., and the pH is adjusted to 7.3 by addition of 16 $\mu$ liter of 1M NaOH. The concentrate is applied on a column of Bio-Gel P-2, 200–400 mesh, bed dimension 2.15 × 70 cm., and is washed in with 3 × 1 ml. washes of deionized water and eluted with deionized water at 0.96 ml./min. Fractions of 3.85 ml. are collected.

The main peak of antibiotic $890A_1$ appears in fractions 24 through 44, with a maximum at fractions 33 and 34. Fractions 27 through 38, having the highest $A_{300}/A_{245}$ ratios, are combined for lyophilization. There combined fractions have a total of 72 $A_{300}$ units.

To carry out the lyophilization, the combined fractions are concentrated to 3.0 ml. and the pH of the concentrate is adjusted to 7.5 by addition of 10$\mu$ liters of 0.1M NaOH. The sample is divided into two portions of 1.50 ml. each, and the portions are separately quick-frozen and lyophilized from 14 ml. glass screw-cap vials. Each sample contains 1.73 mg. of $890A_1$, corresponding to 35.8 $A_{300}$ units.

Compositions containing the antibiotics of the present invention may be administered in several unit dosage forms as, for example, in solid or liquid orally ingestible dosage form. It will be apparent that the antibiotics $890A_1$ and $890A_3$ can be used separately or in combination. The compositions described below apply equally to antibiotics $890A_1$ and $890A_3$ alone and in combination. The compositions per unit dosage, whether liquid or solid may contain from 0.1% to 99% of active material, the preferred range being from about 10 to 60%. The composition will generally contain from about 25 mg. to about 1000 mg. by weight of the active ingredient based upon the total weight of the composition; however, in general, it is preferable to employ a dosage amount in the range of from about 250 mg. to 1000 mg. In parenteral administration the unit dosage is usually the pure compound in a sterile water solution or in the form of a soluble powder intended for solution. Representative formulations can be prepared by the following procedures:

| Capsules | Per Capsule |
| --- | --- |
| Antibiotic $890A_1$ | 400 mg. |

Lactose, U.S.P., a sufficient quantity to fill No 0 Capsules, approx. 475 mg. each In the above example the active compound and the diluent are mixed to produce a uniform blend, which is then filled into No. 0 hard gelatin capsules, by hand or on a suitable machine, as required. The mixing and filling is preferably done in an area having a relative humidity less than 40%.

| Tablets | Per Tablet |
| --- | --- |
| Antibiotic $890A_1$ | 330. mg. |
| Calcium phosphate | 192. mg. |
| Lactose, U.S.P. | 190. mg. |
| Cornstarch | 80. mg. |
| Magnesium stearate | 8. mg. |
|  | 800. mg. |

In the above example, the active component is blended with the calcium phosphate, lactose and about half of the cornstarch. The mixture is granulated with a 15% cornstarch paste and rough-screened and screened again through No. 16 screens. The balance of the cornstarch and the magnesium stearate is added and the mixture is compressed into tablets, approximately ½" in diameter, each weighing 800 mg.

Alternatively, the active component is blended with the calcium phosphate, lactose and one-half the cornstarch. The mixture is "slugged" on a heavy duty press to produce compacted tablet-like masses. These are broken down to a No. 16 mesh granule. The balance of the cornstarch and the magnesium stearate are added and the mixture is compressed into tablets approximately ½" in diameter, each weighing 800 mg.

| Lyo Form (For Injection) | Per Vial |
| --- | --- |
| Antibiotic $890A_1$ | 250 mg. |
| Water-for-Injection, U.S.P. to make | 5 ml. |

In the above example the active component is dissolved in sufficient water-for-injection in the ratio shown. The solution is filtered through Selas candles or Millipore membrane filters to sterilize. The solution is subdivided into sterile vials. The vials and contents are frozen, and the water is aseptically removed by lyophilization. The vials containing the sterile dry solid are aseptically sealed.

To restore for parenteral administration, 5 ml. of sterile water-for-injection is added to the contents of a vial.

| Oral Liquid Forms | Per 1000 ml. |
| --- | --- |
| Antibiotic $890A_1$ | 1.0 gm. |
| Sucrose | 600.0 gm. |
| Glucose | 250.0 gm. |
| Sodium Benzoate | 1.0 gm. |
| Concentrated Orange Oil | 0.2 ml. |
| Purified water U.S.P. to make | 1000.0 ml. |

The sucrose and glucose are dissolved in about 400 ml. of water using heat to aid solution. This solution is cooled and sodium benzoate, followed by the concentrated orange oil added. The solution is brought to about 900 ml. volume with water and the antibiotic is added. The solution is clarified by filtration through a coarse filter.

What is claimed is:

1. The compound 890A₁ having the structure:

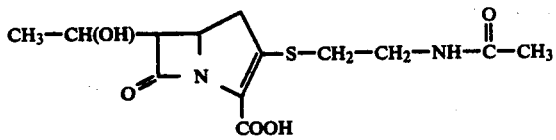

and its pharmaceutically acceptable salts.

2. The compound 890A₃ having the structure:

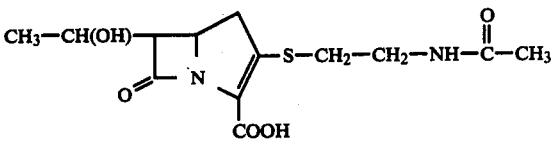

and its pharmaceutically acceptable salts.

3. The mixture comprising compounds 890A₁ and 890A₃.

4. A composition comprising an antibacterial effective amount of the compound 890A₁ and pharmaceutically acceptable salts thereof and a non-toxic pharmaceutically acceptable carrier therefore.

5. A composition comprising an antibacterial effective amount of the compound 890A₃ and pharmaceutically acceptable salts thereof and a non-toxic pharmaceutically acceptable carrier therefore.

6. A composition comprising an antibacterial effective amount of the compound 890A₁ in combination with the compound 890A₃ and pharmaceutically acceptable salts thereof and a non-toxic pharmaceutically acceptable carrier therefore.

* * * * *